United States Patent
Albrecht et al.

(10) Patent No.: US 9,328,117 B2
(45) Date of Patent: May 3, 2016

(54) BROMODOMAIN INHIBITORS AND USES THEREOF

(75) Inventors: Brian K. Albrecht, Cambridge, MA (US); Jean-Christophe Harmange, Andover, MA (US); Alexandre Cote, Cambridge, MA (US); Alexander M. Taylor, Cambridge, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 127 days.

(21) Appl. No.: 14/126,877

(22) PCT Filed: Jun. 15, 2012

(86) PCT No.: PCT/US2012/042825
§ 371 (c)(1),
(2), (4) Date: May 19, 2014

(87) PCT Pub. No.: WO2012/174487
PCT Pub. Date: Dec. 20, 2012

(65) Prior Publication Data
US 2014/0296243 A1   Oct. 2, 2014

Related U.S. Application Data

(60) Provisional application No. 61/498,239, filed on Jun. 17, 2011, provisional application No. 61/540,842, filed on Sep. 29, 2011.

(51) Int. Cl.
*A61K 31/5025* (2006.01)
*C07D 487/04* (2006.01)

(52) U.S. Cl.
CPC .......... *C07D 487/04* (2013.01); *A61K 31/5025* (2013.01)

(58) Field of Classification Search
CPC .......................... A61K 31/5025; C07D 487/04
See application file for complete search history.

(56) References Cited

U.S. PATENT DOCUMENTS

| | | |
|---|---|---|
| 3,523,939 A | 8/1970 | Fryer et al. |
| 3,681,343 A | 8/1972 | Hester, Jr. |
| 3,709,898 A | 1/1973 | Hester, Jr. |
| 3,763,144 A | 10/1973 | Hellerback et al. |
| 3,781,289 A | 12/1973 | Hester, Jr. |
| 3,850,942 A | 11/1974 | Hester et al. |
| 3,886,141 A | 5/1975 | Chase |
| 3,903,103 A | 9/1975 | Hester, Jr. |
| 3,966,736 A | 6/1976 | Szmuszkovicz |
| 4,110,455 A | 8/1978 | von Bebenburg et al. |
| 4,155,904 A | 5/1979 | Schlesinger |
| 4,327,026 A | 4/1982 | Branca et al. |
| 4,374,773 A | 2/1983 | Branca et al. |
| 4,377,522 A | 3/1983 | Branca et al. |
| 4,455,307 A | 6/1984 | Hester, Jr. |
| 4,820,834 A | 4/1989 | Evans et al. |
| 4,959,361 A | 9/1990 | Walser |
| 4,992,437 A | 2/1991 | Naka et al. |
| 5,004,741 A | 4/1991 | Evans et al. |
| 5,175,159 A | 12/1992 | Bock et al. |
| 5,185,331 A | 2/1993 | Freidinger et al. |
| 5,185,442 A | 2/1993 | Weber et al. |
| 5,206,234 A | 4/1993 | Bock et al. |
| 5,382,579 A | 1/1995 | Okano et al. |
| 5,409,909 A | 4/1995 | Okano et al. |
| 5,428,004 A | 6/1995 | Earley et al. |
| 5,439,905 A | 8/1995 | Naka et al. |
| 5,550,126 A | 8/1996 | Horwell et al. |
| 5,593,988 A | 1/1997 | Tahara et al. |
| 5,681,833 A | 10/1997 | Castro Pineiro et al. |
| 5,683,998 A | 11/1997 | Shibayama et al. |
| 5,698,552 A | 12/1997 | Weber et al. |
| 5,712,274 A | 1/1998 | Sueoka et al. |
| 5,721,231 A | 2/1998 | Moriwaki et al. |
| 5,733,905 A | 3/1998 | Albright et al. |
| 5,739,129 A | 4/1998 | Aquino et al. |
| 5,753,647 A | 5/1998 | Weber et al. |
| 5,753,649 A | 5/1998 | Tahara et al. |
| 5,795,887 A | 8/1998 | Aquino et al. |
| 5,840,895 A | 11/1998 | Ohtsuka et al. |
| 5,843,941 A | 12/1998 | Marsters, Jr. et al. |
| 5,869,483 A | 2/1999 | Albright et al. |
| 5,929,069 A | 7/1999 | Shudo |
| 6,121,256 A | 9/2000 | Shudo |

(Continued)

FOREIGN PATENT DOCUMENTS

| | | |
|---|---|---|
| CA | 2020806 A1 | 1/1991 |
| CA | 2032222 A1 | 6/1991 |
| CA | 2032427 A1 | 6/1991 |
| CA | 2050268 A1 | 3/1992 |
| CA | 2056809 A1 | 6/1992 |
| CA | 2059353 A1 | 7/1992 |
| CA | 2062456 A1 | 9/1992 |
| CA | 2071092 A1 | 12/1992 |
| CA | 1327570 C | 3/1994 |
| CA | 02258053 A1 | 12/1997 |
| DE | 2640599 A1 | 3/1978 |
| DE | 3936828 A1 | 5/1990 |
| DE | 4006471 A1 | 9/1990 |
| DE | 4027470 A1 | 3/1992 |
| DE | 4107521 A1 | 9/1992 |
| DE | 4128581 A1 | 3/1993 |
| DE | 4219659 A1 | 12/1993 |
| EP | 0169392 A2 | 1/1986 |

(Continued)

OTHER PUBLICATIONS

PubChemRecord SMR000021202, created Jul. 7, 2005, retrieved from https://pubchem.ncbi.nlm.nih.gov/compound/687922, p. 1-14.*

(Continued)

*Primary Examiner* — Michael Barker
*Assistant Examiner* — Karen Cheng
(74) *Attorney, Agent, or Firm* — McCarter & English LLP; Steven G. Davis; Michael J. DeGrazia

(57) ABSTRACT

The present invention relates to compounds useful as inhibitors of bromodomain-containing proteins. The invention also provides pharmaceutically acceptable compositions comprising compounds of the present invention and methods of using said compositions in the treatment of various disorders.

15 Claims, No Drawings

(56) References Cited

U.S. PATENT DOCUMENTS

| | | |
|---|---|---|
| 6,433,167 B1 | 8/2002 | Fujita et al. |
| 6,458,782 B1 | 10/2002 | Kagechika et al. |
| 6,476,017 B2 | 11/2002 | Shudo |
| 6,649,366 B2 | 11/2003 | Chubinskaya et al. |
| 6,777,408 B1 | 8/2004 | Liberatore et al. |
| 7,015,213 B1 | 3/2006 | Bigg et al. |
| 7,160,880 B1 | 1/2007 | Feldman et al. |
| 7,250,410 B2 | 7/2007 | Bourguignon et al. |
| 7,435,730 B2 | 10/2008 | Feldman et al. |
| 7,442,795 B2 | 10/2008 | Bryans et al. |
| 7,473,689 B2 | 1/2009 | Feldman et al. |
| 7,482,337 B2 | 1/2009 | Himmelsbach et al. |
| 7,485,635 B2 | 2/2009 | Feldman et al. |
| 7,528,127 B2 | 5/2009 | Feldman et al. |
| 7,696,212 B2 | 4/2010 | Himmelsbach et al. |
| 2001/0039272 A1 | 11/2001 | Shudo |
| 2002/0052358 A1 | 5/2002 | Chubinskaya et al. |
| 2004/0053919 A1 | 3/2004 | Chubinskaya et al. |
| 2004/0138214 A1 | 7/2004 | Himmelsbach et al. |
| 2004/0152888 A1 | 8/2004 | Bourguignon et al. |
| 2006/0128695 A1 | 6/2006 | Bourguignon et al. |
| 2007/0093475 A1 | 4/2007 | Feldman et al. |
| 2007/0105844 A1 | 5/2007 | Glick et al. |
| 2007/0135419 A1 | 6/2007 | Feldman et al. |
| 2007/0135420 A1 | 6/2007 | Feldman et al. |
| 2007/0135421 A1 | 6/2007 | Feldman et al. |
| 2009/0093457 A1 | 4/2009 | Himmelsbach et al. |
| 2010/0041643 A1 | 2/2010 | Adachi et al. |
| 2010/0144703 A1 | 6/2010 | Himmelsbach et al. |
| 2010/0256123 A1 | 10/2010 | Sakuma et al. |
| 2010/0286127 A1 | 11/2010 | Miyoshi et al. |
| 2010/0331316 A1 | 12/2010 | Paoletti et al. |
| 2011/0230460 A1 | 9/2011 | Kempen et al. |

FOREIGN PATENT DOCUMENTS

| | | |
|---|---|---|
| EP | 0315698 A1 | 5/1989 |
| EP | 0328924 A2 | 8/1989 |
| EP | 0342587 A2 | 11/1989 |
| EP | 0348523 A1 | 1/1990 |
| EP | 0367110 A1 | 5/1990 |
| EP | 0407955 A1 | 1/1991 |
| EP | 0480455 A1 | 4/1992 |
| EP | 495473 A1 | 7/1992 |
| EP | 0514125 A1 | 11/1992 |
| EP | 0559891 A1 | 9/1993 |
| EP | 0656361 A4 | 1/1995 |
| EP | 636625 A2 | 2/1995 |
| EP | 0661284 A4 | 5/1995 |
| EP | 0692483 A4 | 11/1995 |
| EP | 0989131 A1 | 3/2000 |
| EP | 1297836 A1 | 4/2003 |
| EP | 1887008 A1 | 2/2008 |
| EP | 2239264 A1 | 10/2010 |
| FR | 2154511 A1 | 5/1973 |
| FR | 2220257 A1 | 10/1974 |
| GB | 1409693 A | 10/1975 |
| GB | 2259013 A | 3/1993 |
| JP | 7179471 | 7/1995 |
| JP | 11228576 | 8/1999 |
| JP | 2959591 B2 | 10/1999 |
| JP | 3223290 B2 | 10/2001 |
| JP | 03264588 B2 | 3/2002 |
| JP | 03264589 B2 | 3/2002 |
| JP | 04226993 B2 | 2/2009 |
| WO | 9303717 A1 | 3/1993 |
| WO | 9307129 A1 | 4/1993 |
| WO | 9312791 A1 | 7/1993 |
| WO | 9313776 A1 | 7/1993 |
| WO | 9319052 A1 | 9/1993 |
| WO | 9406801 A1 | 3/1994 |
| WO | 9426723 A2 | 11/1994 |
| WO | 9514694 A1 | 6/1995 |
| WO | 9528399 A1 | 10/1995 |
| WO | 9711061 A1 | 3/1997 |
| WO | 9747622 A1 | 12/1997 |
| WO | 9811111 A1 | 3/1998 |
| WO | 9828268 A2 | 7/1998 |
| WO | 9858930 A1 | 12/1998 |
| WO | 9929324 A1 | 6/1999 |
| WO | 0006157 A1 | 2/2000 |
| WO | 0012547 A2 | 3/2000 |
| WO | 0054778 A1 | 9/2000 |
| WO | 0069836 A1 | 11/2000 |
| WO | 0147510 A2 | 7/2001 |
| WO | 02098865 A2 | 12/2002 |
| WO | 03/074525 A1 | 9/2003 |
| WO | 2004041258 A2 | 5/2004 |
| WO | 2004041820 A1 | 5/2004 |
| WO | 2004/058769 A2 | 7/2004 |
| WO | 2005/002590 A1 | 1/2005 |
| WO | 2005099759 A1 | 10/2005 |
| WO | 2006038560 A1 | 4/2006 |
| WO | 2006129623 A1 | 12/2006 |
| WO | 2007016087 A2 | 2/2007 |
| WO | 2007050587 A2 | 5/2007 |
| WO | 2007/079820 A1 | 7/2007 |
| WO | 2008023847 A1 | 2/2008 |
| WO | 2008109856 A2 | 9/2008 |
| WO | 2009059191 A1 | 5/2009 |
| WO | 2009081349 A1 | 7/2009 |
| WO | 2009152589 A1 | 12/2009 |
| WO | 2010008459 A1 | 1/2010 |
| WO | 2010049466 A1 | 5/2010 |
| WO | 2010121164 A2 | 10/2010 |
| WO | 2010128685 A1 | 11/2010 |
| WO | 2011037128 A1 | 3/2011 |
| WO | 2011054553 A1 | 5/2011 |
| WO | 2011054841 A1 | 5/2011 |
| WO | 2011054843 A1 | 5/2011 |
| WO | 2011054844 A1 | 5/2011 |
| WO | 2011054845 A1 | 5/2011 |
| WO | 2011054846 A1 | 5/2011 |
| WO | 2011054848 A1 | 5/2011 |
| WO | 2011054851 A1 | 5/2011 |
| WO | 2011079315 A1 | 6/2011 |
| WO | 2011/123678 A2 | 10/2011 |
| WO | 2011143651 A1 | 11/2011 |
| WO | 2011143657 A1 | 11/2011 |
| WO | 2011143660 A2 | 11/2011 |
| WO | 2011143669 A2 | 11/2011 |
| WO | 2011/161031 A1 | 12/2011 |
| WO | 2012/075383 A2 | 6/2012 |
| WO | 2013024104 A1 | 2/2013 |
| WO | 2013030150 A1 | 3/2013 |
| WO | 2013033268 A2 | 3/2013 |
| WO | 2013033269 A1 | 3/2013 |
| WO | 2013033270 A2 | 3/2013 |
| WO | 2013033420 A1 | 3/2013 |

OTHER PUBLICATIONS

Iegraverend, 1981, J. Heterocyclic Chem, vol. 18, No. 893, p. 893-898.*

Grey, R., et al., "Structure-Based Design of 3-aryl-6-amino-triazolo[4,3-b]pyridazine Inhibitors of Pim-1 Kinase," Bioorg. Med. Chem. Lett., Jun. 1, 2009, vol. 19, No. 11, pp. 3019-3022.

International Preliminary Report on Patentability, mailed Jan. 3, 2014, International Application No. PCT/US2012/042825; International Filing Date: Jun. 15, 2012, 10 pages.

Proctor, George R., et al., "Azabenzycycloheptones, Part 19, Formation of Some Heterocyclic Annulated Compounds from 1,2,3,4-tetrahydro-1-benzazepine derivatives," Journal of the Chemical Society, Perkin Transactions 1, Chemical Society, Letchworth, GB, Jan. 1, 1978, pp. 862-879.

Venkateswarlu, Peesapati, et al., "Synthesis and Biological Activity of Some New Heterocyclic Annelated Compounds from 2,3,4,5-tetrahydro-1-benzazepines," Indian Journal of Chemistry: IJC, Council of Scientific and Industrial Research, IN., vol. 35B, Dec. 1, 1996, pp. 1287-1293.

Filippakopoulos, et al., "Selective Inhibition of BET Bromodomains," Nature, Dec. 30, 2010, vol. 468, pp. 1067-1073.

(56) References Cited

OTHER PUBLICATIONS

Kosychova, L., et al., "Synthesis of Substitute 5,6-Dihydro-4H-[1,2,4]Triazolo[4,3-a][1,5]Benzodiazepines," Chemistry of Heterocyclic Compounds, vol. 40, No. 6, Jun. 2004, pp. 811-815.
Gussio, Rick, et al., "All-Atom Models for the Non-Nucleoside Binding Site of HIV-1 Reverse Transcriptase Complexed with Inhibitors: A 3D QSAR Approach," J. Med. Chem., Apr. 12, 1996, vol. 39, No. 8, pp. 1645-1650.
International Search Report and Written Opinion, dated Jul. 23, 2013, Int'l Appl'n No. PCT/US2013/044449, Int'l Filing Date Jun. 6, 2013.
International Search Report and Written Opinion, dated Feb. 21, 2013, Int'l Appl'n No. PCT/US2012/042825, Int'l Filing Date Jun. 15, 2012.
International Preliminary Report on Patentability, dated Nov. 5, 2013, Int'l Appl'n No. PCT/US2012/036569, Int'l Filing Date May 4, 2012.
International Search Report and Written Opinion, dated Jul. 23, 2013, Int'l Appl'n No. PCT/US2013/044444, Int'l Filing Date Jun. 6, 2013.
International Search Report and Written Opinion, dated Apr. 17, 2012, Int'l Appl'n No. PCT/US2011/063173, Int'l Filing Date Dec. 2, 2011.
Terrett, N.K., et al., "Imidazoú2',3':6,5 3/4 Dipyridoú3,2-B:2',3'-E 3/4-1,4-Diazepines: Non-Nucleoside HIV-1 Reverse Transcriptase Inhibitors with Greater Enzyme Affinity than Nevirapine," Bioorganic & Medicinal Chemistry Letters, vol. 12, No. 2, Dec. 1, 1992, pp. 1745-1750, XP002912883.
Kosychova, et al., "Synthesis of New [1,2,4]triazolo[4,3-a][1,5]benzodiaze-pine derivatives," Lietuvos Mokslu Akademija. Chemija, vol. 22, No. 1, Jan. 1, 2011, pp. 60-64, XP055136653.
Kosychova, et al., "Synthesis of novel 5,6-dihydro-4H-[1,2,4] triazolo[4,3-a][1,5]benzodiazepines," Rigas Tehniskas Universitates Zinatniskie Raksti. Serija 1: Materialzinatne Un Lietiska Kimija, vol. 22, Jan. 1, 2010, pp. 94-99, XP009179817.
Di Bracco, M., et al., "1,5-Benzodiazepines. Part XII. Synthesis and Biological Evaluations of Tricyclic and Tetracyclic 1,5-benzodiazepine Derivatives as Nevirapine Analogues," European Journal of Medicinal Chemistry, vol. 36, No. 11-12, Dec. 1, 2001, pp. 935-949, XP027205317.
Jiban K. Chakrabarti, et al., "Chemistry of Adamantane. Part XI. 1,2-Disubstituted Adamantanes. Synthesis and Reactions of Adamantano[2,1-b]- and protoadamantano-[4,5-b][1,5]benzodiazepines," Journal of Heterocyclic Chemistry, vol. 15, No. 5, Aug. 1, 1978, pp. 705-710, XP055136791.
Szarvasi, E., et al., "(4H)Dihydro-5,6(s)-triazolo-(4,3-a)benzodiazepines-1,5 a activite analgesique et anti-inflammatoire," European Journal of Medicinal Chemistry, vol. 13, No. 2, Mar. 1, 1978, pp. 113-119, XP009179828.

\* cited by examiner

BROMODOMAIN INHIBITORS AND USES THEREOF

CROSS-REFERENCE TO RELATED APPLICATIONS

This application is a 35 U.S.C. §371 national stage filing of International Application No. PCT/US2012/042825, filed Jun. 15, 2012, which claims the benefit of U.S. Provisional Application No. 61/498,239, filed Jun. 17, 2011 and U.S. Provisional Application No. 61/540,842, filed Sep. 29, 2011. The entire contents of each of the afore-mentioned applications are incorporated herein by reference.

TECHNICAL FIELD OF THE INVENTION

The present invention relates to compounds useful as inhibitors of one or more bromodomain-containing proteins.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin: the defining template for gene regulation. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding proteins or chromatin-modifying enzymes. Significantly, an increasing number of these proteins have been associated with a variety of disorders such as neurodegenerative disorders, metabolic diseases, inflammation, and cancer. Thus, highly selective therapeutic agents directed against this emerging class of gene regulatory proteins promise new approaches to the treatment of human diseases.

SUMMARY OF THE INVENTION

In one aspect, the invention provides a compound of formula I:

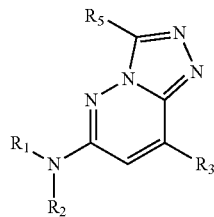

I or a pharmaceutically acceptable salt, prodrug, solvate, or hydrate thereof, wherein:

$R_1$ is optionally substituted aralkyl, optionally substituted heteroarylalkyl, optionally substituted alkenyl, optionally substituted alkynyl, optionally substituted aryl, optionally substituted cycloalkyl, optionally substituted heteroaryl, optionally substituted heterocycloalkyl, haloalkyl, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —C=NN(R')(R"), —C=NOR, or —C(=N(R'))N(R')(R");

$R_2$ is H, optionally substituted alkyl, optionally substituted alkenyl, optionally substituted alkynyl, optionally substituted aryl, optionally substituted aralkyl, optionally substituted heteroarylalkyl, optionally substituted cycloalkyl, optionally substituted heteroaryl, optionally substituted heterocycloalkyl, haloalkyl, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —C=NN(R')(R"), —C=NOR, —C(=N(R'))N(R')(R"), or —(CH$_2$)$_p$R$_x$; or $R_1$ and $R_2$ together with the atoms to which each is attached, forms an optionally substituted 3-7 membered saturated or unsaturated ring having 0-4 additional heteroatoms independently selected from nitrogen, oxygen, or sulfur; wherein the ring is optionally substituted by -alkyl, -alkenyl, -alkynyl, -aryl, -arylalkyl, -heteroaryl, -heteroarylalkyl, -heterocycloalkyl, -cycloalkyl, -carbocyclic, -heterocyclic, —F, —Cl, —Br, —I, —OH, protected hydroxy, alkoxy, oxo, thiooxo, —NO$_2$, —CN, CF$_3$, N$_3$, —NH$_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl;

$R_3$ is H, alkyl, alkenyl, alkynyl, aralkyl, aryl, cycloalkyl, heteroaryl, heterocycloalkyl, or halo, each of which is optionally substituted; or CN, OR$_A$, NR$_A$R$_B$, N(R$_A$)S(O)$_q$R$_A$R$_B$, N(R$_A$)C(O)R$_B$, N(R$_A$)C(O)NR$_A$R$_B$, N(R$_A$)C(O)OR$_A$, N(R$_A$)C(S)NR$_A$R$_B$, —N(R$_A$)S(O)$_q$NR$_A$R$_B$, S(O)$_q$R$_A$, C(O)R$_A$, C(O)OR$_A$, OC(O)R$_A$, or C(O)NR$_A$R$_B$;

each $R_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each $R_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or $R_A$ and $R_B$, together with the atoms to which each is attached, can form a heterocycloalkyl or a heteroaryl; each of which is optionally substituted;

$R_5$ is halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, haloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N (R'))N(R')(R"), —C═NN(R')(R"), —C═NOR, —C(═N(R'))N(R')(R"), —OC(O)R, —OC(O)N(R')(R"), or —(CH$_2$)$_p$R$_x$;

each R$_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(═N(R'))N(R')(R"), —C═NN(R')(R"), —C═NOR, —C(═N(R'))N(R')(R"), —OC(O)R, —OC(O)N(R')(R");

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group;

each R" is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted;

each p is independently 1, 2, 3, 4, 5, or 6; and
each q is independently 0, 1, or 2;

wherein, when R$_1$ is optionally substituted cycloalkyl, optionally substituted aralkyl, or optionally substituted heteroarylalkyl, then R$_5$ is not CF$_3$;

wherein the compound is not one of the following:
4-((methyl(3-methyl-[1,2,4]triazolo[4,3-b]pyridazin-6-yl)amino)methyl)benzamide;
3-(6-(benzyl(methyl)amino)-[1,2,4]triazolo[4,3-b]pyridazin-3-yl)-1-(piperidin-1-yl)propan-1-one;
3-(6-(benzyl(methyl)amino)-[1,2,4]triazolo[4,3-b]pyridazin-3-yl)-1-morpholinopropan-1-one; N-benzyl-3-ethyl-N-methyl-[1,2,4]triazolo[4,3-b]pyridazin-6-amine;
N-benzyl-3-isopropyl-N-methyl-[1,2,4]triazolo[4,3-b]pyridazin-6-amine; and
4-((6-(cyclohexyl(methyl)amino)-[1,2,4]triazolo[4,3-b]pyridazin-3-yl)methyl)phenol.

In another aspect, the invention provides a compound of formula IA:

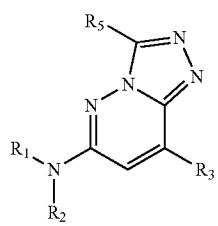

I or a pharmaceutically acceptable salt, prodrug, solvate, or hydrate thereof, wherein:

R$_1$ is optionally substituted aralkyl, optionally substituted heteroarylalkyl, optionally substituted alkenyl, optionally substituted alkynyl, optionally substituted aryl, optionally substituted cycloalkyl, optionally substituted heteroaryl, optionally substituted heterocycloalkyl, haloalkyl, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —C═NN(R')(R"), —C═NOR, or —C(═N(R'))N(R')(R");

R$_2$ is H, optionally substituted alkyl, optionally substituted alkenyl, optionally substituted alkynyl, optionally substituted aryl, optionally substituted aralkyl, optionally substituted heteroarylalkyl, optionally substituted cycloalkyl, optionally substituted heteroaryl, optionally substituted heterocycloalkyl, haloalkyl, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —C═NN(R')(R"), —C═NOR, —C(═N(R'))N(R')(R"), or —(CH$_2$)$_p$R$_x$; or R$_1$ and R$_2$ together with the atoms to which each is attached, forms an optionally substituted 3-7 membered saturated or unsaturated ring having 0-4 additional heteroatoms independently selected from nitrogen, oxygen, or sulfur; wherein the ring is optionally substituted by -alkyl, -alkenyl, -alkynyl, -aryl, -arylalkyl, -heteroaryl, -heteroarylalkyl, -heterocycloalkyl, -cycloalkyl, -carbocyclic, -heterocyclic, —F, —Cl, —Br, —I, —OH, protected hydroxy, alkoxy, oxo, thiooxo, —NO$_2$, —CN, CF$_3$, N$_3$, —NH$_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl;

R$_3$ is H, alkyl, alkenyl, alkynyl, aralkyl, aryl, cycloalkyl, heteroaryl, heterocycloalkyl, or halo, each of which is optionally substituted; or CN, OR$_A$, NR$_A$R$_B$, N(R$_A$)S(O)$_q$R$_A$R$_B$, N(R$_A$)C(O)R$_B$, N(R$_A$)C(O)NR$_A$R$_B$, N(R$_A$)C(O)OR$_A$, N(R$_A$)C(S)NR$_A$R$_B$, —N(R$_A$)S(O)$_q$NR$_A$R$_B$, S(O)$_q$R$_A$, C(O)R$_A$, C(O)OR$_A$, OC(O)R$_A$, or C(O)NR$_A$R$_B$;

each R$_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each R$_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or R$_A$ and R$_B$, together with the atoms to which each is attached, can form a heterocycloalkyl or a heteroaryl; each of which is optionally substituted;

R$_5$ is halogen, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, haloalkyl, —OR, —SR, —CN, —N(R')

(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R"), or —(CH$_2$)$_p$R$_x$;

each R$_x$ is independently hydrogen, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group;

each R" is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted;

each p is independently 1, 2, 3, 4, 5, or 6; and each q is independently 0, 1, or 2;

wherein, when R$_2$ is H and R$_1$ is optionally substituted cycloalkyl, optionally substituted aralkyl, or optionally substituted heteroarylalkyl, then R$_5$ is not CF$_3$, phenyl, or —CH$_2$CH$_2$CO$_2$H;

wherein the compound is not one of the following:

4-((methyl(3-methyl-[1,2,4]triazolo[4,3-b]pyridazin-6-yl)amino)methyl)benzamide;

3-(6-(benzyl(methyl)amino)-[1,2,4]triazolo[4,3-b]pyridazin-3-yl)-1-(piperidin-1-yl)propan-1-one;

3-(6-(benzyl(methyl)amino)-[1,2,4]triazolo[4,3-b]pyridazin-3-yl)-1-morpholinopropan-1-one; N-benzyl-3-ethyl-N-methyl-[1,2,4]triazolo[4,3-b]pyridazin-6-amine;

N-benzyl-3-isopropyl-N-methyl-[1,2,4]triazolo[4,3-b]pyridazin-6-amine; and 4-((6-(cyclohexyl(methyl)amino)-[1,2,4]triazolo[4,3-b]pyridazin-3-yl)methyl)phenol.

In another aspect, the invention provides for a composition comprising a compound described herein (e.g., any formulae herein), and a pharmaceutically acceptable adjuvant, carrier, or vehicle.

In another aspect, the invention provides a method for inhibiting activity of a bromodomain-containing protein, or a mutant thereof, in a biological sample comprising the step of contacting said biological sample with a compound of the invention (e.g., any formulae herein).

In another aspect, the invention provides a method for inhibiting activity of a bromodomain-containing protein, or a mutant thereof, in a patient comprising the step of administering to said patient a compound of the invention (e.g., any formulae herein).

In another aspect, the invention provides a method for treating a bromodomain-containing protein-mediated disorder in a patient in need thereof, comprising the step of administering to said patient a compound of the invention (e.g., any formulae herein).

Provided compounds, and pharmaceutically acceptable compositions thereof, are useful for treating a variety of diseases, disorders or conditions associated with abnormal cellular responses triggered by events mediated by bromodomain-containing proteins. Such diseases, disorders, or conditions include those described herein.

Provided compounds are also useful for the study of bromodomain-containing proteins in biological and pathological phenomena, the study of intracellular signal transduction pathways mediated by bromodomain-containing proteins, and the comparative evaluation of new inhibitors of bromodomain-containing proteins.

DETAILED DESCRIPTION

Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof. The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The number of carbon atoms in a hydrocarbyl substituent can be indicated by the prefix "$C_x$-$C_y$," where x is the minimum and y is the maximum number of carbon atoms in the substituent.

The prefix "halo" indicates that the substituent to which the prefix is attached is substituted with one or more independently selected halogen radicals. For example, "haloalkyl" means an alkyl substituent wherein at least one hydrogen radical is replaced with a halogen radical.

If a linking element in a depicted structure is "absent", then the left element in the depicted structure is directly linked to the right element in the depicted structure. For example, if a chemical structure is depicted as X-L-Y wherein L is absent, then the chemical structure is X—Y.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I). The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Aliphatic groups include, but are not limited to, alkyl, alkenyl, alkynyl, carbocycle. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 18 carbon ring atoms, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, the term "cycloalkylene" refers to a bivalent cycloalkyl group. In certain embodiments, a cycloalkylene group is a 1,1-cycloalkylene group (i.e., a spiro-fused ring). Exemplary 1,1-cycloalkylene groups include

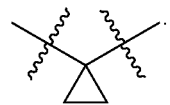 [SMILES: *C1(*)CC1]

In other embodiments, a cycloalkylene group is a 1,2-cycloalkylene group or a 1,3-cycloalkylene group. Exemplary 1,2-cycloalkylene groups include

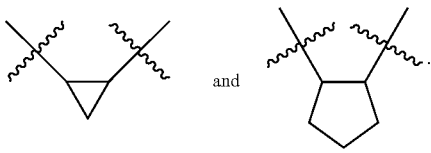 [SMILES: *C1CC1* ; *C1CCCC1*]

The term "alkyl" as used herein, refers to a saturated, straight- or branched-chain hydrocarbon radical typically containing from 1 to 20 carbon atoms. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_2$-$C_8$ alkynyl" contains from two to eight carbon atoms.

Representative alkynyl groups include, but are not limited to, for example, ethynyl, 1-propynyl, 1-butynyl, heptynyl, octynyl and the like.

The term "aryl" used alone or as part of a larger moiety as in "aralkyl", "aralkoxy", or "aryloxyalkyl", refers to monocyclic, bicyclic, and tricyclic ring systems having a total of five to 15 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. The term "aralkyl" or "arylalkyl" refers to an alkyl residue attached to an aryl ring. Examples of aralkyl include, but are not limited to, benzyl, phenethyl and the like. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 18 ring atoms, preferably 5, 6, or 9 ring atoms; having 6, 10, or 14 π electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

As used herein, the terms "heterocycle", "heterocyclyl", "heterocyclic radical", and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "bivalent hydrocarbon" refers to a bivalent saturated or unsaturated hydrocarbon group. Such bivalent hydrocarbon groups include alkylene, alkenylene, and alkynylene groups.

The term "alkylene" refers to a divalent group derived from a straight or branched saturated hydrocarbyl chain typically containing from 1 to 20 carbon atoms, more typically from 1 to 8 carbon atoms. Examples of an "alkylene" include a polymethylene group, i.e., —$(CH_2)_n$—, wherein n is a positive integer, preferably from 1 to 6, from 1 to 4, from 1 to 3, from 1 to 2, or from 2 to 3; or —$CH_2$—, —$CH_2CH_2$—, —$CH_2CH_2CH_2$—, —$CH_2CH_2CH_2CH_2$—, and —$CH_2CH(CH_3)CH_2$—. A substituted alkylene chain is a polymethylene group in which one or more methylene hydrogen atoms are replaced with a substituent. Suitable substituents include those described below for a substituted aliphatic group.

The term "alkenylene" refers to a divalent unsaturated hydrocarbyl group which may be linear or branched and which has at least one carbon-carbon double bond. An alkenylene group typically contains 2 to 20 carbon atoms, more typically from 2 to 8 carbon atoms. Non-limiting examples of alkenylene groups include —C(H)=C(H)—, —C(H)=C(H)—$CH_2$—, —C(H)=C(H)—$CH_2$—$CH_2$—, —$CH_2$—C(H)=C(H)—$CH_2$—, —C(H)=C(H)—CH($CH_3$)—, and —$CH_2$—C(H)=C(H)—CH($CH_2CH_3$)—.

The term "alkynylene" refers to a divalent unsaturated hydrocarbon group which may be linear or branched and which has at least one carbon-carbon triple bond. Representative alkynylene groups include, by way of example, —C≡C—, —C≡C—$CH_2$—, —C≡C—$CH_2$—$CH_2$—, —$CH_2$—C≡C—$CH_2$—, —C≡C—CH($CH_3$)—, and —$CH_2$—C≡C—CH($CH_2CH_3$)—. The definitions of various alkyl, alkenyl, alkynyl, aralkyl, etc. groups above (e.g., propyl, butyl, pentyl, hexyl, etc.) contemplate all linear and branched variants (e.g., n-butyl, i-butyl, t-butyl).

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl," "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy, alkoxy, oxo, thiooxo,

—$NO_2$, —CN, $CF_3$, $N_3$,

—$NH_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$-heterocycloalkyl, —NHC(O)$NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, NHC(S)$NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)$NH_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl-$SO_2NH_2$, —$SO_2$NH-alkyl, —$SO_2$NH-alkenyl, —$SO_2$NH-alkynyl, —$SO_2$NH-cycloalkyl, —$SO_2$NH-aryl, —$SO_2$NH-heteroaryl, —$SO_2$NH-heterocycloalkyl, —$NHSO_2$-alkyl, —$NHSO_2$-alkenyl, —$NHSO_2$-alkynyl, —$NHSO_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$, a. -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

In certain embodiments, suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}$—CH$(OR°)_2$; —$(CH_2)_{0-4}SR°$; —$(CH_2)_{0-4}$Ph, which may be substituted with R°; —$(CH_2)_{0-4}O(CH_2)_{0-1}$Ph which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —N(R°)C(S)R°; —$(CH_2)_{0-4}$N (R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched)alkylene)O—N(R°$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below. Suitable monovalent substituents on R° (or the ring formed by taking two independent occurrences of R° together with their intervening atoms), are independently halogen, —(CH$_2$)$_{0-2}$R˙, -(haloR˙), —(CH$_2$)$_{0-2}$OH, —(CH$_2$)$_{0-2}$OR˙, —(CH$_2$)$_{0-2}$CH(OR˙)$_2$, —O(haloR˙), —CN, —N$_3$, —(CH$_2$)$_{0-2}$C(O)R˙, —(CH$_2$)$_{0-2}$C(O)OH, —(CH$_2$)$_{0-2}$C(O)OR˙, —(CH$_2$)$_{0-2}$SR˙, —(CH$_2$)$_{0-2}$SH, —(CH$_2$)$_{0-2}$NH$_2$, —(CH$_2$)$_{0-2}$NHR˙, —(CH$_2$)$_{0-2}$NR˙$_2$, —NO$_2$, —SiR˙$_3$, —OSiR˙$_3$, —C(O)SR˙, —(C$_{1-4}$ straight or branched alkylene)C(O)OR˙, or —SSR˙ wherein each R˙ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "suitable amino protecting group," includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10, 10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

As used herein, the term "inhibitor" is defined as a compound that binds to and/or inhibits the target bromodomain-containing protein (such as a BET protein, e.g., BRD2, BRD3, BRD4, and/or BRDT) with measurable affinity. In certain embodiments, an inhibitor has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Description Of Exemplary Compounds

In one aspect, the invention provides a compound of formula I:

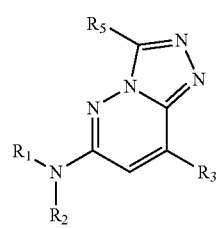

I or a pharmaceutically acceptable salt, prodrug, solvate, or hydrate thereof, wherein:

$R_1$ is optionally substituted aralkyl, optionally substituted heteroarylalkyl, optionally substituted alkenyl, optionally substituted alkynyl, optionally substituted aryl, optionally substituted cycloalkyl, optionally substituted heteroaryl, optionally substituted heterocycloalkyl, haloalkyl, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —C=NN(R')(R"), —C=NOR, or —C(=N(R'))N(R')(R");

$R_2$ is H, optionally substituted alkyl, optionally substituted alkenyl, optionally substituted alkynyl, optionally substituted aryl, optionally substituted aralkyl, optionally substituted heteroarylalkyl, optionally substituted cycloalkyl, optionally substituted heteroaryl, optionally substituted heterocycloalkyl, haloalkyl, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —C=NN(R')(R"), —C=NOR, —C(=N(R'))N(R')(R"), or —(CH$_2$)$_p$R$_x$; or $R_1$ and $R_2$ together with the atoms to which each is attached, forms an optionally substituted 3-7 membered saturated or unsaturated ring having 0-4 additional heteroatoms independently selected from nitrogen, oxygen, or sulfur; wherein the ring is optionally substituted by -alkyl, -alkenyl, -alkynyl, -aryl, -arylalkyl, -heteroaryl, -heteroarylalkyl, -heterocycloalkyl, -cycloalkyl, -carbocyclic, -heterocyclic, —F, —Cl, —Br, —I, —OH, protected hydroxy, alkoxy, oxo, thiooxo, —NO$_2$, —CN, CF$_3$, N$_3$, —NH$_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl;

$R_3$ is H, alkyl, alkenyl, alkynyl, aralkyl, aryl, cycloalkyl, heteroaryl, heterocycloalkyl, or halo, each of which is optionally substituted; or CN, OR$_A$, NR$_A$R$_B$, N(R$_A$)S(O)$_q$R$_A$R$_B$, N(R$_A$)C(O)R$_B$, N(R$_A$)C(O)NR$_A$R$_B$, N(R$_A$)C(O)OR$_A$, N(R$_A$)C(S)NR$_A$R$_B$, —N(R$_A$)S(O)$_q$NR$_A$R$_B$, S(O)$_q$R$_A$, C(O)R$_A$, C(O)OR$_A$, OC(O)R$_A$, or C(O)NR$_A$R$_B$;

each $R_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each $R_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or $R_A$ and $R_B$, together with the atoms to which each is attached, can form a heterocycloalkyl or a heteroaryl; each of which is optionally substituted;

$R_5$ is halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, haloalkyl, —OR, —SR, —CN, —N(R')(R"), —C(O)R, —C(S)R, —CO₂R, —C(O)N(R')(R"), —C(O)SR, —C(O)C(O)R, —C(O)CH₂C(O)R, —C(S)N(R')(R"), —C(S)OR, —S(O)R, —SO₂R, —SO₂N(R')(R"), —N(R')C(O)R, —N(R')C(O)N(R')(R"), —N(R')C(S)N(R')(R"), —N(R')SO₂R, —N(R')SO₂N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R"), or —(CH₂)ₚRₓ;

each Rₓ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO₂R, —C(O)N(R')(R"), —C(O)SR, —C(O)C(O)R, —C(O)CH₂C(O)R, —C(S)N(R')(R"), —C(S)OR, —S(O)R, —SO₂R, —SO₂N(R')(R"), —N(R')C(O)R, —N(R')C(O)N(R')(R"), —N(R')C(S)N(R')(R"), —N(R')SO₂R, —N(R')SO₂N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —CO₂R, —C(O)N(R)₂, —C(S)N(R)₂, —S(O)R, —SO₂R, —SO₂N(R)₂, or two R groups on the same nitrogen are taken together with their intervening atoms to form an optionally substituted heteroaryl or heterocycloalkyl group;

each R" is independently —R, —C(O)R, —C(S)R, —CO₂R, —C(O)N(R)₂, —C(S)N(R)₂, —S(O)R, —SO₂R, —SO₂N(R)₂, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted;

each p is independently 1, 2, 3, 4, 5, or 6; and each q is independently 0, 1, or 2;

wherein, when R₁ is optionally substituted cycloalkyl, optionally substituted aralkyl, or optionally substituted heteroarylalkyl, then R₅ is not CF₃;

wherein the compound is not one of the following:

4-((methyl(3-methyl-[1,2,4]triazolo[4,3-b]pyridazin-6-yl)amino)methyl)benzamide;

3-(6-(benzyl(methyl)amino)-[1,2,4]triazolo[4,3-b]pyridazin-3-yl)-1-(piperidin-1-yl)propan-1-one;

3-(6-(benzyl(methyl)amino)-[1,2,4]triazolo[4,3-b]pyridazin-3-yl)-1-morpholinopropan-1-one; N-benzyl-3-ethyl-N-methyl-[1,2,4]triazolo[4,3-b]pyridazin-6-amine;

N-benzyl-3-isopropyl-N-methyl-[1,2,4]triazolo[4,3-b]pyridazin-6-amine; and 4-((6-(cyclohexyl(methyl)amino)-[1,2,4]triazolo[4,3-b]pyridazin-3-yl)methyl)phenol.

In another aspect, the invention provides a compound of formula IA:

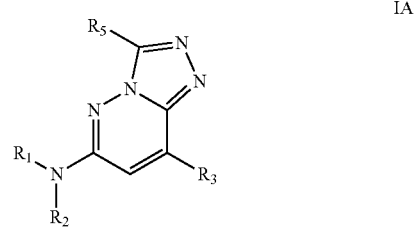

IA or a pharmaceutically acceptable salt, prodrug, solvate, or hydrate thereof, wherein:

R₁ is optionally substituted aralkyl, optionally substituted heteroarylalkyl, optionally substituted alkenyl, optionally substituted alkynyl, optionally substituted aryl, optionally substituted cycloalkyl, optionally substituted heteroaryl, optionally substituted heterocycloalkyl, haloalkyl, —C(O)R, —C(S)R, —CO₂R, —C(O)N(R')(R"), —C(O)SR, —C(O)C(O)R, —C(O)CH₂C(O)R, —C(S)N(R')(R"), —C(S)OR, —S(O)R, —SO₂R, —SO₂N(R')(R"), —C=NN(R')(R"), —C=NOR, or —C(=N(R'))N(R')(R");

R₂ is H, optionally substituted alkyl, optionally substituted alkenyl, optionally substituted alkynyl, optionally substituted aryl, optionally substituted aralkyl, optionally substituted heteroarylalkyl, optionally substituted cycloalkyl, optionally substituted heteroaryl, optionally substituted heterocycloalkyl, haloalkyl, —C(O)R, —C(S)R, —CO₂R, —C(O)N(R')(R"), —C(O)SR, —C(O)C(O)R, —C(O)CH₂C(O)R, —C(S)N(R')(R"), —C(S)OR, —S(O)R, —SO₂R, —SO₂N(R')(R"), —C=NN(R')(R"), —C=NOR, —C(=N(R'))N(R')(R"), or —(CH₂)ₚRₓ; or R₁ and R₂ together with the atoms to which each is attached, forms an optionally substituted 3-7 membered saturated or unsaturated ring having 0-4 additional heteroatoms independently selected from nitrogen, oxygen, or sulfur; wherein the ring is optionally substituted by -alkyl, -alkenyl, -alkynyl, -aryl, -arylalkyl, -heteroaryl, -heteroarylalkyl, -heterocycloalkyl, -cycloalkyl, -carbocyclic, -heterocyclic, —F, —Cl, —Br, —I, —OH, protected hydroxy, alkoxy, oxo, thiooxo, —NO₂, —CN, CF₃, N₃, —NH₂, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl;

R₃ is H, alkyl, alkenyl, alkynyl, aralkyl, aryl, cycloalkyl, heteroaryl, heterocycloalkyl, or halo, each of which is optionally substituted; or CN, OR_A, NR_AR_B, N(R_A)S(O)_qR_AR_B, N(R_A)C(O)R_B, N(R_A)C(O)NR_AR_B, N(R_A)C(O)OR_A, N(R_A)C(S)NR_AR_B, —N(R_A)S(O)_qNR_AR_B, S(O)_qR_A, C(O)R_A, C(O)OR_A, OC(O)R_A, or C(O)NR_AR_B;

each R_A is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each $R_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or $R_A$ and $R_B$, together with the atoms to which each is attached, can form a heterocycloalkyl or a heteroaryl; each of which is optionally substituted;

$R_5$ is halogen, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, haloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R"), or —(CH$_2$)$_p$R$_x$;

each $R_x$ is independently hydrogen, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group;

each R" is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted;

each p is independently 1, 2, 3, 4, 5, or 6; and each q is independently 0, 1, or 2;

wherein, when $R_2$ is H and $R_1$ is optionally substituted cycloalkyl, optionally substituted aralkyl, or optionally substituted heteroarylalkyl, then $R_5$ is not CF$_3$, phenyl, or —CH$_2$CH$_2$CO$_2$H;

wherein the compound is not one of the following:

4-((methyl(3-methyl-[1,2,4]triazolo[4,3-b]pyridazin-6-yl)amino)methyl)benzamide;

3-(6-(benzyl(methyl)amino)-[1,2,4]triazolo[4,3-b]pyridazin-3-yl)-1-piperidin-1-yl)propan-1-one;

3-(6-(benzyl(methyl)amino)-[1,2,4]triazolo[4,3-b]pyridazin-3-yl)-1-morpholinopropan-1-one;

N-benzyl-3-ethyl-N-methyl-[1,2,4]triazolo[4,3-b]pyridazin-6-amine;

N-benzyl-3-isopropyl-N-methyl-[1,2,4]triazolo[4,3-b]pyridazin-6-amine; and 4-((6-(cyclohexyl(methyl)amino)-[1,2,4]triazolo[4,3-b]pyridazin-3-yl)methyl)phenol.

In one embodiment, $R_1$ is optionally substituted aralkyl, optionally substituted heteroarylalkyl, optionally substituted aryl, optionally substituted cycloalkyl, optionally substituted heteroaryl, optionally substituted heterocycloalkyl, or haloalkyl. In a further embodiment, $R_1$ is optionally substituted aralkyl, optionally substituted heteroarylalkyl, or optionally substituted cycloalkyl.

In another embodiment, $R_2$ is H, optionally substituted alkyl, optionally substituted aryl, optionally substituted aralkyl, optionally substituted cycloalkyl, optionally substituted heteroaryl, optionally substituted heterocycloalkyl, haloalkyl, or —(CH$_2$)$_p$R$_x$.

In certain embodiments, $R_1$ and $R_2$ together with the atoms to which each is attached, forms an optionally substituted 3-7 membered saturated or unsaturated ring having 1-4 additional heteroatoms independently selected from nitrogen, oxygen, or sulfur. In various embodiments, $R_3$ is H, OR$_A$, NR$_A$R$_B$, N(R$_C$)S(O)$_q$R$_A$R$_B$, N(R$_A$)C(O)R$_B$, N(R$_A$)C(O)NR$_A$R$_B$, N(R$_A$)C(O)OR$_A$, N(R$_A$)C(S)NR$_A$R$_B$, or OC(O)R$_A$.

In certain embodiments, $R_5$ is halogen, optionally substituted alkenyl, optionally substituted alkynyl, haloalkyl, —CN, or —(CH$_2$)$_p$R$_x$, wherein $R_x$ is hydrogen or optionally substituted alkyl. In certain embodiments, when $R_2$ is H and $R_1$ is optionally substituted cycloalkyl, optionally substituted aralkyl, or optionally substituted heteroarylalkyl, then $R_5$ is not trihalo-substituted alkyl, aryl, or -alkyl-CO$_2$H In certain embodiments, $R_2$ is H, methyl, or —(CH$_2$)$_p$R$_x$.

In a further embodiment, $R_x$ is H, —N(R')(R"), —C(O)R, —C(S)R, —CO$_2$R, —C(O)N(R')(R"), —C(S)N(R')(R"), —S(O)R, —SO$_2$R, —SO$_2$N(R')(R"), —N(R')C(O)R, —N(R')SO$_2$R, —OC(O)R, —OC(O)N(R')(R"), methyl, ethyl, propyl, i-propyl, butyl, s-butyl, pentyl or hexyl.

In certain embodiments, $R_5$ is —(CH$_2$)$_p$R$_x$. In one embodiment, $R_5$ is H, methyl, or CF$_3$. In a further embodiment, $R_x$ is —N(R')(R"), —C(O)R, —C(S)R, —CO$_2$R, —C(O)N(R')(R"), —C(S)N(R')(R"), —S(O)R, —SO$_2$R, —SO$_2$N(R')(R"), —N(R')C(O)R, —N(R')SO$_2$R, —OC(O)R, —OC(O)N(R')(R"), methyl, ethyl, propyl, i-propyl, butyl, s-butyl, pentyl or hexyl.

In another embodiment, the invention provides a compound of formula II:

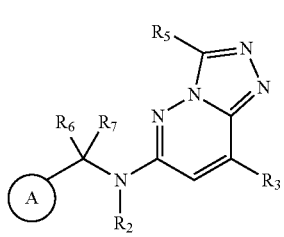

II or a pharmaceutically acceptable salt, prodrug, solvate, or hydrate thereof, wherein:

ring A is optionally substituted aryl or optionally substituted heteroaryl;

$R_6$ is H or optionally substituted alkyl;

R$_7$ is H or optionally substituted alkyl; or

R$_6$ and R$_7$, together with the atom to which each is attached, forms a carbocyclic or heterocyclic, each of which is optionally substituted;

R$_2$ is H, optionally substituted alkyl, optionally substituted aryl, optionally substituted aralkyl, optionally substituted cycloalkyl, optionally substituted heteroaryl, optionally substituted heterocycloalkyl, haloalkyl, or —(CH$_2$)$_p$R$_x$; or R$_2$ and R$_6$, together with the atoms to which each is attached, form a heterocyclic or heteroaryl ring, each of which is optionally substituted;

R$_3$ is H, OR$_A$, NR$_A$R$_B$, N(R$_A$)S(O)$_q$R$_A$R$_B$, N(R$_A$)C(O)R$_B$, N(R$_A$)C(O)NR$_A$R$_B$, N(R$_A$)C(O)OR$_A$, N(R$_A$)C(S)NR$_A$R$_B$, or OC(O)R$_A$;

each R$_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each R$_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or R$_A$ and R$_B$, together with the atoms to which each is attached, can form a heterocycloalkyl or a heteroaryl; each of which is optionally substituted;

R$_5$ is Me, Et, Pr, CF$_3$, CH$_2$CF$_3$, CF$_2$CF$_3$, CN, F, Cl, Br, I, optionally substituted alkynyl;

each R$_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R''), —C(O)R, —C(S)R, —CO$_2$R, —C(O)N(R')(R''), —C(O)SR, —C(O)C(O)R, —C(O)CH$_2$C(O)R, —C(S)N(R')(R''), —C(S)OR, —S(O)R, —SO$_2$R, —SO$_2$N(R')(R''), —N(R')C(O)R, —N(R')C(O)N(R')(R''), —N(R')C(S)N(R')(R''), —N(R')SO$_2$R, —N(R')SO$_2$N(R')(R''), —N(R')N(R')(R''), —N(R')C(=N(R'))N(R')(R''), —C=NN(R')(R''), —C=NOR, —C(=N(R'))N(R')(R''), —OC(O)R, —OC(O)N(R')(R'');

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; and each R'' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; or R' and R'', together with the atoms to which each is attached, can form a cycloalkyl, a heterocycloalkyl, an aryl, or a heteroaryl; each of which is optionally substituted.

In certain embodiments, ring A is phenyl, napthyl, pyridyl, pyrimidinyl, pyrazinyl, pyridazinyl, furyl, thiophenyl, pyrrolo, isoxazolyl, or isothiazolyl; each of which is optionally substituted. In a further embodiment, ring A is phenyl, pyridyl, furyl, or thiophenyl, each of which is optionally substituted.

In other embodiments, R$_6$ is methyl, ethyl, propyl, butyl, pentyl, or hexyl; each of which is optionally substituted. In a further embodiment, R$_6$ is methyl.

In various embodiments, R$_2$ is H, methyl, ethyl, propyl, butyl, pentyl, hexyl, phenyl, or napthyl; each of which is optionally substituted.

In still other embodiments, R$_3$ is H, OR$_A$, NR$_A$R$_B$, N(R$_A$)C(O)R$_B$, N(R$_A$)C(O)OR$_A$, or OC(O)R$_A$.

In still other embodiments, R$_3$ is N(R$_A$)C(O)NR$_A$R$_B$.

In another embodiment, the invention provides a compound of formula III:

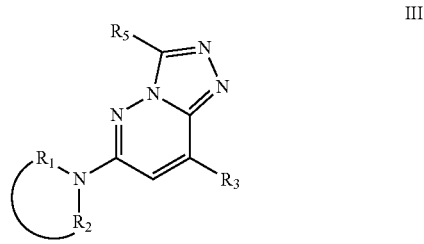

or a pharmaceutically acceptable salt, prodrug, solvate, or hydrate thereof, wherein:

the ring formed by R$_1$ and R$_2$ together with the atoms to which each is attached, forms an optionally substituted 3-7 membered saturated or unsaturated ring having 0-4 additional heteroatoms independently selected from nitrogen, oxygen, or sulfur;

R$_3$ is H, OR$_A$, NR$_A$R$_B$, N(R$_A$)S(O)$_q$R$_A$R$_B$, N(R$_A$)C(O)R$_B$, N(R$_A$)C(O)NR$_A$R$_B$, N(R$_A$)C(O)OR$_A$, N(R$_A$)C(S)NR$_A$R$_B$, or OC(O)R$_A$;

each R$_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each R$_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or R$_A$ and R$_B$, together with the atoms to which each is attached, can form a heterocycloalkyl or a heteroaryl; each of which is optionally substituted;

R$_5$ is —(CH$_2$)$_p$R$_x$, CF$_3$, —CF$_2$CF$_3$, CN, F, Cl, Br, I, optionally substituted alkynyl;

each R$_x$ is independently hydrogen, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R''), —C(O)R, —C(S)R, —CO$_2$R, —C(O)N(R')(R''), —C(O)SR, —C(O)C(O)R, —C(O)CH$_2$C(O)R, —C(S)N(R')(R''), —C(S)OR, —S(O)R, —SO$_2$R, —SO$_2$N(R')(R''), —N(R')C(O)R, —N(R')C(O)N(R')(R''), —N(R')C(S)N(R')(R''), —N(R')SO$_2$R, —N(R')SO$_2$N(R')(R''), —N(R')N(R')(R''), —N(R')C(=N(R'))N(R')(R''), —C=NN(R')(R''), —C=NOR, —C(=N(R'))N(R')(R''), —OC(O)R, —OC(O)N(R')(R'');

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; and each R" is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted; and p is 1, 2, or 3.

In certain embodiments, the ring formed by $R_1$ and $R_2$ together with the atoms to which each is attached, forms a pyrrolidine, piperidine, pyrazolidine, piperazine, morpholine, isoxolidine, pyridyl, pyrimidinyl, pyrazinyl, azetidine, lactam, cyclic urea, or pyridazinyl; each of which is optionally substituted. In certain embodiments, the ring is pyrrolidine, or piperidine. In various embodiments, the ring formed by $R_1$ and $R_2$ is optionally substituted by -alkyl, -alkenyl, -alkynyl, -aryl, -arylalkyl, -heteroaryl, -heteroarylalkyl, -heterocycloalkyl, -cycloalkyl, -carbocyclic, -heterocyclic, —F, —Cl, —Br, —I, —OH, protected hydroxy, alkoxy, oxo, thiooxo, —NO$_2$, —CN, CF$_3$, N$_3$, —NH$_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl. In various embodiments, $R_3$ is H, OR$_A$, NR$_A$R$_B$, N(R$_A$)C(O)R$_B$, or OC(O)R$_A$.

In certain embodiments, $R_5$ is Me, Et, Pr, —CH$_2$CF$_3$, —CF$_3$, CF$_2$CF$_3$, CN, F, Cl, Br, I, or optionally substituted alkynyl;

In certain embodiments, $R_5$ is Me.

In another embodiment, the invention provides a compound of formula IV:

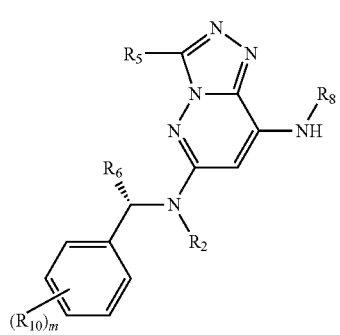

IV or a pharmaceutically acceptable salt thereof, wherein:
$R_2$ is optionally substituted alkyl;
$R_5$ is —(CH$_2$)$_p$R$_x$, wherein R$_x$ is hydrogen or optionally substituted alkyl;
$R_6$ is optionally substituted alkyl;
$R_8$ is selected from hydrogen, —C(O)NR$_A$R$_B$ and —C(O)OR$_A$, wherein each of R$_A$ and R$_B$ is independently selected from hydrogen or alkyl;
each $R_{10}$ is an independently selected substituent (as discussed in detail supra.);
p is 1, 2, 3, 4, 5, or 6; and
m is 0, 1, 2 or 3.

In certain embodiments of Formula IV, $R_2$ is methyl.
In certain embodiments of Formula IV, $R_5$ is methyl.
In certain embodiments of Formula IV, $R_6$ is methyl.
In certain embodiments of Formula IV, $R_8$ is selected from hydrogen, —C(O)—N(CH$_3$)$_2$, —C(O)—NH—CH$_2$CH$_3$, and —C(O)—O—CH$_2$CH$_3$.

In certain embodiments, $R_{10}$, each independently, is alkyl or halo.

In certain embodiments of Formula IV, m is 0 or 1.

In one embodiment, when m is 1, $R_{10}$ is a para substituent. In another embodiment, when m is 1, $R_{10}$ is a para substituent selected from chloro and fluoro.

In other embodiments, the invention provides a compound selected from Table 1:

TABLE 1

Exemplary Compounds of the Invention

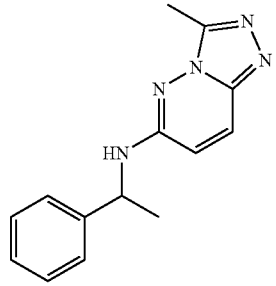 [SMILES: Cc1nnc2ccc(NC(C)c3ccccc3)nn12]

1

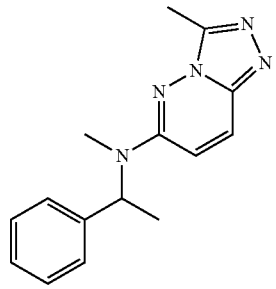 [SMILES: Cc1nnc2ccc(N(C)C(C)c3ccccc3)nn12]

2

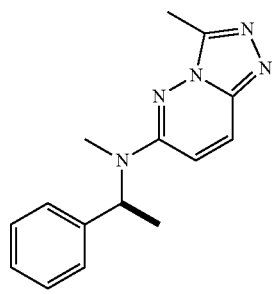 [SMILES: Cc1nnc2ccc(N(C)[C@@H](C)c3ccccc3)nn12]

3

TABLE 1-continued
Exemplary Compounds of the Invention
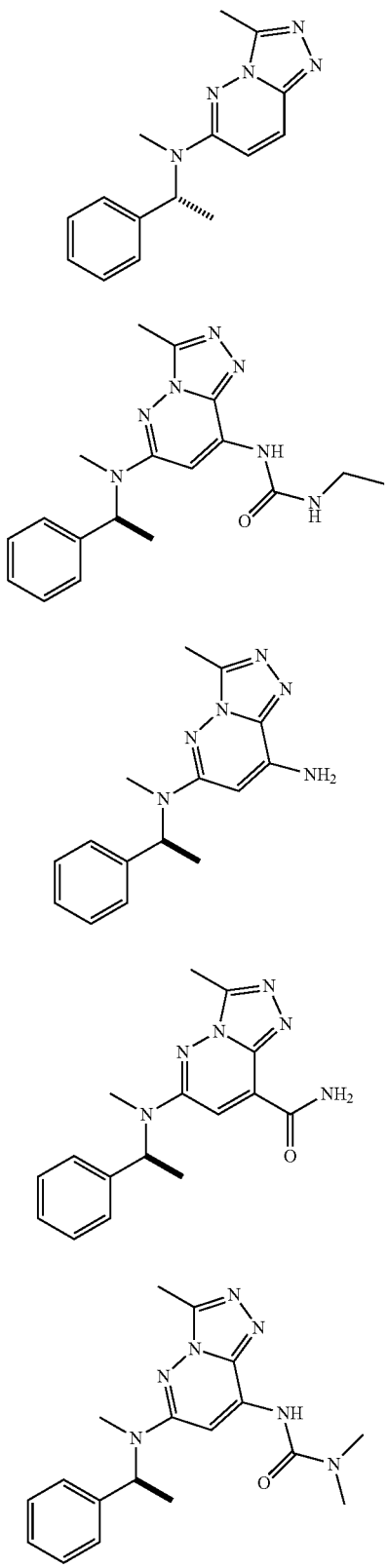
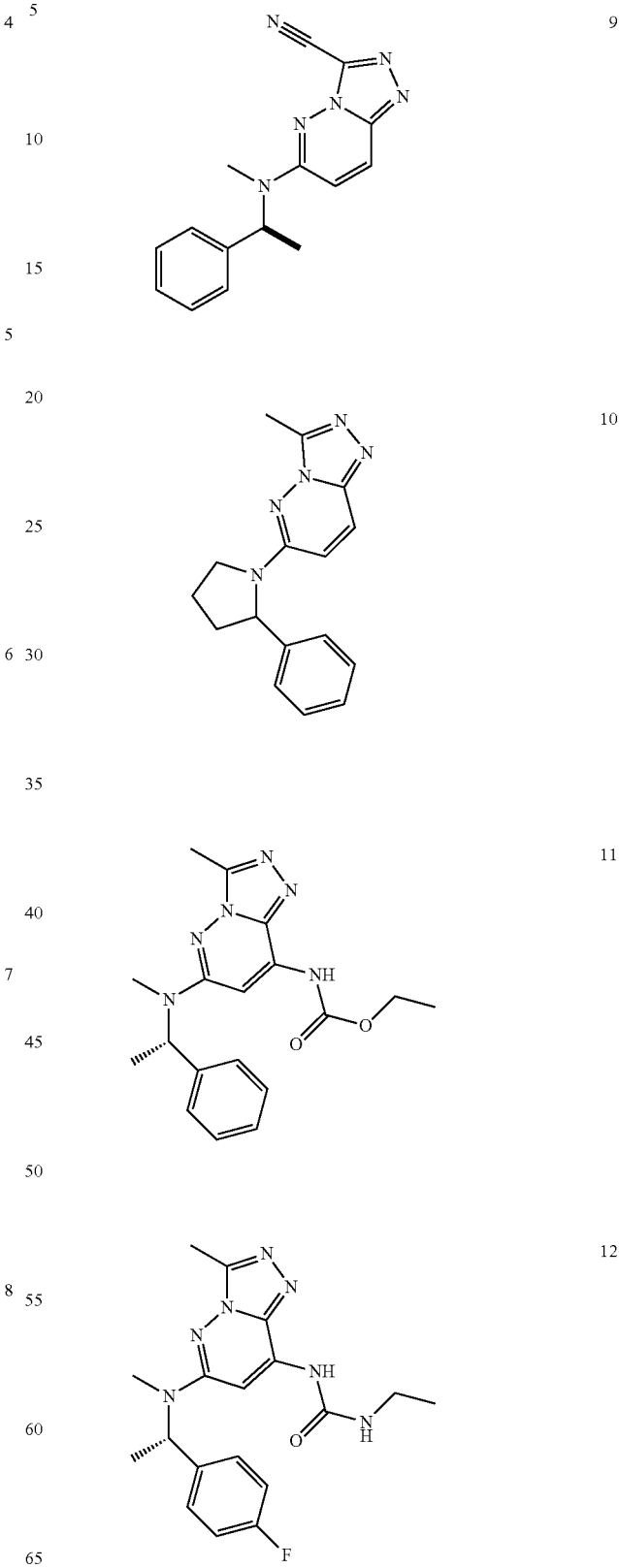

TABLE 1-continued

Exemplary Compounds of the Invention

13

[Chemical structure of compound 13]

14

[Chemical structure of compound 14]

In another aspect, the invention provides a composition comprising a compound as described herein (e.g., a compound of formula I or IA) and a pharmaceutically acceptable adjuvant, carrier, or vehicle.

In one embodiment, the invention provides a composition in combination with an additional therapeutic agent.

In certain embodiments, the present invention provides a method of inhibiting a bromodomain-containing protein (such as a BET protein, e.g., BRD2, BRD3, BRD4, and/or BRDT) comprising contacting said bromodomain-containing protein with any compound as described herein (e.g., a compound of formula I or IA) or a compound depicted in Table 1, above, or a pharmaceutically acceptable salt or composition thereof.

Uses, Formulation and Administration; Pharmaceutically Acceptable Compositions

In another aspect, the invention provides for a composition comprising a compound of any of the formulae herein, and a pharmaceutically acceptable adjuvant, carrier, or vehicle.

In one embodiment, the invention provides for a composition, in combination with an additional therapeutic agent.

According to another embodiment, the present invention provides a method of inhibiting a bromodomain-containing protein (such as a BET protein, e.g., BRD2, BRD3, BRD4, and/or BRDT) using a composition comprising a compound of the invention or a pharmaceutically acceptable derivative thereof and a pharmaceutically acceptable carrier, adjuvant, or vehicle. The amount of a compound of the invention in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, the amount of compound in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, a provided composition is formulated for administration to a patient in need of such composition. In some embodiments, a provided composition is formulated for oral administration to a patient.

The term "patient," as used herein, means an animal, such as a mammal, such as a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitory active metabolite or residue thereof.

As used herein, the term "inhibitory active metabolite or residue thereof" means that a metabolite or residue thereof is also an inhibitor of one or more bromodomain-containing proteins (such as a BET protein, e.g., BRD2, BRD3, BRD4, and/or BRDT), or a mutant thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

In another aspect, the invention provides a method for inhibiting activity of a bromodomain-containing protein, or a mutant thereof, in a biological sample comprising the step of contacting said biological sample with a compound as described herein (e.g. any formulae herein).

In one embodiment, the bromodomain-containing protein is a BET protein.

In a further embodiment, the BET protein is BRD4.

In another aspect, the invention provides a method for inhibiting activity of a bromodomain-containing protein, or a mutant thereof, in a patient comprising the step of administering to said patient a compound as described herein (e.g. any formulae herein).

In one embodiment, the bromodomain-containing protein is a BET protein.

In other embodiments, the BET protein is BRD4.

In another aspect, the invention provides a method for treating a bromodomain-containing protein-mediated disorder in a patient in need thereof, comprising the step of administering to said patient a compound as described herein (e.g. any formulae herein).

In one embodiment, the bromodomain-containing protein is a BET protein.

In a further embodiment, the BET protein is BRD4.

In another embodiment, the disorder is a proliferative disorder, inflammatory disease, sepsis, autoimmune disease, or viral infection.

In a further embodiment, the proliferative disorder is cancer.

In certain embodiments, the cancer is adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

Compounds and compositions described herein are generally useful for the inhibition of activity of one or more proteins involved in epigenetic regulation. Thus, in some embodiments, the present invention provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a provided compound or composition.

Epigenetics is the study of heritable changes in gene expression caused by mechanisms other than changes in the underlying DNA sequence. Molecular mechanisms that play a role in epigenetic regulation include DNA methylation and chromatin/histone modifications. Chromatin recognition, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) *Curr. Opin. Genet. Dev.* 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) *Nature* 389:251-260). Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

One type of histone modification, lysine acetylation, is recognized by bromodomain-containing proteins. Bromodomain-containing proteins are components of transcription factor complexes and determinants of epigenetic memory (Dey, et al. (2009) *Mol. Biol. Cell* 20:4899-4909). There are 46 human proteins containing a total of 57 bromodomains discovered to date. One family of bromodomain-containing proteins, BET proteins (BRD2, BRD3, BRD4, and BRDT) have been used to establish proof-of-concept for targeting protein-protein interactions of epigenetic "readers," as opposed to chromatin-modifying enzymes, or so-called epigenetic "writers" and "erasers" (Filippakopoulos, et al. "Selective Inhibition of BET Bromodomains," *Nature* (published online Sep. 24, 2010); Nicodeme, et al. "Suppression of Inflammation by a Synthetic Histone Mimic," *Nature* (published online Nov. 10, 2010)).

Examples of proteins inhibited by the compounds and compositions described herein and against which the methods described herein are useful include bromodomain-containing proteins, such as BET proteins, such as BRD2, BRD3, BRD4, and/or BRDT, or an isoform or mutant thereof.

The activity of a provided compound, or composition thereof, as an inhibitor of a bromodomain-containing protein, such as a BET protein, such as BRD2, BRD3, BRD4, and/or BRDT, or an isoform or mutant thereof, may be assayed in vitro, in vivo, or in a cell line. In vitro assays include assays that determine inhibition of bromodomain-containing proteins, such as BET proteins, such as BRD2, BRD3, BRD4, and/or BRDT, or a mutant thereof. Alternatively, inhibitor binding may be determined by running a competition experiment where a provided compound is incubated with a bromodomain-containing protein, such as a BET protein, such as BRD2, BRD3, BRD4, and/or BRDT bound to known ligands, labeled or unlabeled. Detailed conditions for assaying a provided compound as an inhibitor of a bromodomain-containing protein, such as a BET protein, such as BRD2, BRD3, BRD4, and/or BRDT or a mutant thereof, are set forth in the Examples below. The invention provides for a method of treating a subject with a MYC-dependent cancer, comprising: identifying a subject in need of treatment; administering to the subject a BET inhibitor; determining at least one of MYC mRNA expression, MYC protein expression and tumor mass, and wherein following administration, there is a decrease in at least one of myc mRNA expression, MYC protein expression and tumor mass, thereby treating the disease.

In one embodiment, the identification step comprises determining whether the subject has at least one of a MYC translocation, a genetic rearrangement of MYC, MYC amplification, MYC over-expression and at least one cellular function that facilitates cellular and/or tumor growth and is altered upon reduction of myc mRNA or protein expression.

The invention also provides for a method of treating a subject with a MYC-dependent cancer, comprising: determining in a subject at least one of MYC mRNA expression, MYC protein expression and tumor mass; administering to the subject a BET inhibitor; and comparing at least one of MYC mRNA expression, MYC protein expression and tumor mass in the subject before and after administration of the BET inhibitor.

The invention also provides a method of treating a subject with a MYC-dependent cancer, comprising: administering to the subject a BET inhibitor that is identified as capable of decreasing at least one of myc mRNA expression, MYC protein expression and tumor mass; and determining at least one of myc mRNA expression, MYC protein expression and tumor mass; wherein following the administration, there is a decrease in at least one of myc mRNA expression, MYC protein expression and tumor mass, thereby treating the disease.

The invention also provides for a method of treating a subject with a disease, comprising: administering a BET inhibitor that is identified as capable of decreasing at least one of myc mRNA expression, MYC protein expression and tumor mass, wherein following the administration, there is a decrease in at least one of myc mRNA expression, MYC protein expression and tumor mass, thereby treating the disease.

Acetylated histone recognition and bromodomain-containing proteins (such as BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/G1, including growth-associated genes, and remains bound to chromatin throughout the cell cycle (Dey, et al. (2009) *Mol. Biol. Cell* 20:4899-4909). BRD4 also physically associates with Mediator and P-TEFb (CDK9/cyclin T1) to facilitate transcriptional elongation (Yang, et al. (2005) *Oncogene* 24:1653-1662; Yang, et al. (2005) *Mol. Cell.* 19:535-545). CDK9 is a validated target in chronic lymphocytic leukemia (CLL), and is linked to c-Myc-dependent transcription (Phelps, et al. *Blood* 113:2637-2645; Rahl, et al. (2010) *Cell* 141:432-445).

BRD4 is translocated to the NUT protein in patients with lethal midline carcinoma, an aggressive form of human squamous carcinoma (French, et al. (2001) *Am. J. Pathol.* 159: 1987-1992; French, et al. (2003) *Cancer Res.* 63:304-307). In vitro analysis with RNAi supports a causal role for BRD4 in this recurrent t(15;19) chromosomal translocation. Pharmacologic inhibition of the BRD4 bromodomains results in growth arrest/differentiation of BRD4-NUT cell lines in vitro and in vivo (Filippakopoulos, et al. "Selective Inhibition of BET Bromodomains," *Nature* (published online Sep. 24, 2010)).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression (Hargreaves, et al. (2009) *Cell* 138:129-145; LeRoy, et al. (2008) *Mol. Cell.* 30:51-60; Jang, et al. (2005) *Mol. Cell.* 19:523-534; Yang, et al. (2005) *Mol. Cell.* 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme, et al. "Suppression of Inflammation by a Synthetic Histone Mimic," *Nature* (published online Nov. 10, 2010)). Bromodomain-containing proteins (such as BET proteins) also play a role in viral disease. For example, BRD4 is implicated in human papilloma virus (HPV). In the primary phase of HPV infection of basal epithelia, the viral genome is maintained in an extra-chromosomal episome. In some strains of HPV, BRD4 binding to the HPV E2 protein functions to tether the viral genome to chromosomes. E2 is critical for both the repression of E6/E7 and to activation of HPV viral genes. Disruption of BRD4 or the BRD4-E2 interaction blocks E2-dependent gene activation. BRD4 also functions to tether other classes of viral genomes to host chromatin (e.g., Herpesvirus, Epstein-Ban virus).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In certain embodiments, a provided compound inhibits one or more of BRD2, BRD3, BRD4, BRDT, and/or another member of the bromodomain-containing proteins, or a mutant thereof. In some embodiments, a provided compound inhibits two or more of BRD2, BRD3, BRD4, BRDT, and/or another member of the bromodomain-containing proteins, or a mutant thereof. Provided compounds are inhibitors of one or more of the bromodomain-containing proteins, such as BRD2, BRD3, BRD4, and/or BRDT and are therefore useful for treating one or more disorders associated with activity of one or more of the bromodomain-containing proteins, such as BRD2, BRD3, BRD4, and/or BRDT. Thus, in certain embodiments, the present invention provides a method for treating an bromodomain-containing protein-mediated disorder, such as a BET-mediated, a BRD2-mediated, a BRD3-mediated, a BRD4-mediated disorder, and/or a BRDT-mediated disorder comprising the step of inhibiting a bromodomain-containing protein, such as a BET protein, such as BRD2, BRD3, BRD4, and/or BRDT, or a mutant thereof, by administering to a patient in need thereof a provided compound, or a pharmaceutically acceptable composition thereof.

As used herein, the terms "bromodomain-containing protein-mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role. Accordingly, another embodiment of the present invention relates to treating or lessening the severity of one or more diseases in which one or more of the bromodomain-containing proteins, such as BET proteins, such as BRD2, BRD3, BRD4, and/or BRDT, or a mutant thereof, are known to play a role.

Diseases and conditions treatable according to the methods of this invention include, but are not limited to, cancer and other proliferative disorders, inflammatory diseases, sepsis, autoimmune disease, and viral infection. Thus one aspect is a method of treating a subject having a disease, disorder, or symptom thereof the method including administration of a compound or composition herein to the subject. In one embodiment, a human patient is treated with a compound of the invention and a pharmaceutically acceptable carrier, adjuvant, or vehicle, wherein said compound is present in an amount to measurably inhibit bromodomain-containing protein activity (such as BET protein, e.g., BRD2, BRD3, BRD4, and/or BRDT) in the patient. The invention further relates to a method for treating or ameliorating cancer or another proliferative disorder by administration of an effective amount of a compound according to this invention to a mammal, in particular a human in need of such treatment. In some aspects of the invention, the disease to be treated by the methods of the present invention is cancer. Examples of cancers treated using the compounds and methods described herein include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In some embodiments, the present invention provides a method of treating a benign proliferative disorder. Such benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome. The invention further relates to a method for treating infectious and noninfectious inflammatory events and autoimmune and other inflammatory diseases by administration of an effective amount of a provided compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease. In some embodiments, the present invention provides a method of treating systemic inflammatory response syndromes such as LPS-induced endotoxic shock and/or bacteria-induced sepsis by administration of an effective amount of a provided compound to a mammal, in particular a human in need of such treatment.

The invention further relates to a method for treating viral infections and diseases by administration of an effective amount of a provided compound to a mammal, in particular a human in need of such treatment. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

The invention further provides a method of treating a subject, such as a human, suffering from one of the abovementioned conditions, illnesses, disorders or diseases. The method comprises administering a therapeutically effective amount of one or more provided compounds, which function by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The invention further provides a therapeutic method of modulating protein methylation, gene expression, cell proliferation, cell differentiation and/or apoptosis in vivo in diseases mentioned above, in particular cancer, inflammatory disease, and/or viral disease comprising administering to a subject in need of such therapy a pharmacologically active and therapeutically effective amount of one or more provided compounds.

The invention further provides a method of regulating endogenous or heterologous promoter activity by contacting a cell with a provided compound.

In certain embodiments, the invention provides a method of treating a disorder (as described above) in a subject, comprising administering to the subject identified as in need thereof, a compound of the invention. The identification of those patients who are in need of treatment for the disorders described above is well within the ability and knowledge of one skilled in the art. Certain of the methods for identification of patients which are at risk of developing the above disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a disorder by methods well known in the art (e.g., determining tumor size or screening for tumor markers where the cell proliferative disorder is cancer) and then administering a therapeutically effective amount of a compound of the invention, to the subject. After an appropriate period of time after the administration of the compound (e.g., 1 day, 1 week, 2 weeks, one month, six months), the extent of the disorder is determined again. The modulation (e.g., decrease) of the extent or invasiveness of the disorder indicates efficacy of the treatment. The extent or invasiveness of the disorder may be determined periodically throughout treatment. For example, the extent or invasiveness of the disorder may be checked every few hours, days or weeks to assess the further efficacy of the treatment. A decrease in extent or invasiveness of the disorder indicates that the treatment is efficacious. The method described may be used to screen or select patients that may benefit from treatment with a compound of the invention.

The invention further relates to the use of provided compounds for the production of pharmaceutical compositions which are employed for the treatment and/or prophylaxis and/or amelioration of the diseases, disorders, illnesses and/or conditions as mentioned herein.

The invention further relates to the use of provided compounds for the production of pharmaceutical compositions which are employed for the treatment and/or prophylaxis of diseases and/or disorders responsive or sensitive to the inhibition of bromodomain-containing proteins, particularly those diseases mentioned above, such as e.g. cancer, inflammatory disease, viral disease.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

Compounds or compositions described herein may be administered using any amount and any route of administration effective for treating or lessening the severity of cancer or other proliferative disorder. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. Pharmaceutically acceptable compositions of this disclosure can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. According to some embodiments, the invention relates to a method of inhibiting bromodomain-containing proteins in a biological sample comprising the step of contacting said biological sample with a provided compound, or a composition thereof.

According to some embodiments, the invention relates to a method of inhibiting a bromodomain-containing protein, such as a BET protein, such as BRD2, BRD3, BRD4 and/or BRDT, or a mutant thereof, activity in a biological sample comprising the step of contacting said biological sample with a provided compound, or a composition thereof.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of activity of an protein, e.g., a bromodomain-containing protein, such as a BET protein, such as BRD2, BRD3, BRD4 and/or BRDT, or a mutant thereof, in a biological sample is useful for a variety of purposes that are known to one of skill in the art. Examples of such purposes include, but are not limited to, blood transfusion, organ-transplantation, biological specimen storage, and biological assays. According to another embodiment, the invention relates to a method of inhibiting activity of one or more bromodomain-containing protein, such as a BET protein, such as BRD2, BRD3, BRD4, and/or BRDT, or a mutant thereof, in a patient comprising the step of administering to said patient a provided compound, or a composition comprising said compound. In certain embodiments, the present invention provides a method for treating a disorder mediated by one or more bromodomain-containing proteins, such as a BET protein, such as BRD2, BRD3, BRD4, and/or BRDT, or a mutant thereof, in a patient in need thereof, comprising the step of administering to said patient a provided compound or pharmaceutically acceptable composition thereof. Such disorders are described in detail herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the additional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

Other therapies, chemotherapeutic agents, or other antiproliferative agents may be combined with a provided compound to treat proliferative diseases and cancer. Examples of therapies or anticancer agents that may be used in combination with compounds of formula I or IA include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effects (e.g., an antiemetic), and any other approved chemotherapeutic drug.

A provided compound may also be used to advantage in combination with one or more antiproliferative compounds. Such antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Exemplary aromatase inhibitors include steroids, such as atamestane, exemestane and formestane, and non-steroids, such as aminoglutethimide, rogletimide, pyridoglutethimide, trilostane, testolactone, ketoconazole, vorozole, fadrozole, anastrozole and letrozole.

Exemplary anti-estrogens include tamoxifen, fulvestrant, raloxifene and raloxifene hydrochloride. Anti-androgens include, but are not limited to, bicalutamide. Gonadorelin agonists include, but are not limited to, abarelix, goserelin and goserelin acetate.

Exemplary topoisomerase I inhibitors include topotecan, gimatecan, irinotecan, camptothecin and its analogues, 9-nitrocamptothecin and the macromolecular camptothecin conjugate PNU-166148. Topoisomerase II inhibitors include, but are not limited to, the anthracyclines such as doxorubicin, daunorubicin, epirubicin, idarubicin and nemorubicin, the anthraquinones mitoxantrone and losoxantrone, and the podophillotoxins etoposide and teniposide.

Exemplary microtubule active agents include microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof. Exemplary alkylating agents include cyclophosphamide, ifosfamide, melphalan or nitrosoureas such as carmustine and lomustine.

Exemplary cyclooxygenase inhibitors include Cox-2 inhibitors, 5-alkyl substituted 2-arylaminophenylacetic acid and derivatives, such as celecoxib, rofecoxib, etoricoxib, valdecoxib or a 5-alkyl-2-arylaminophenylacetic acid, such as lumiracoxib.

Exemplary matrix metalloproteinase inhibitors ("MMP inhibitors") include collagen peptidomimetic and non-peptidomimetic inhibitors, tetracycline derivatives, batimastat, marimastat, prinomastat, metastat, BMS-279251, BAY 12-9566, TAA211, MMI270B, and AAJ996.

Exemplary mTOR inhibitors include compounds that inhibit the mammalian target of rapamycin (mTOR) and possess antiproliferative activity such as sirolimus, everolimus, CCI-779, and ABT578.

Exemplary antimetabolites include 5-fluorouracil (5-FU), capecitabine, gemcitabine, DNA demethylating compounds, such as 5-azacytidine and decitabine, methotrexate and edatrexate, and folic acid antagonists such as pemetrexed.

Exemplary platin compounds include carboplatin, cis-platin, cisplatinum, and oxaliplatin.

Exemplary methionine aminopeptidase inhibitors include bengamide or a derivative thereof and PPI-2458.

Exemplary bisphosphonates include etidronic acid, clodronic acid, tiludronic acid, pamidronic acid, alendronic acid, ibandronic acid, risedronic acid and zoledronic acid. Exemplary antiproliferative antibodies include trastuzumab, trastuzumab-DM1, cetuximab, bevacizumab, rituximab, PRO64553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary heparanase inhibitors include compounds that target, decrease or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras; for example, a farnesyl transferase inhibitor such as L-744832, DK8G557, tipifarnib, and lonafarnib.

Exemplary telomerase inhibitors include compounds that target, decrease or inhibit the activity of telomerase, such as compounds which inhibit the telomerase receptor, such as telomestatin.

Exemplary proteasome inhibitors include compounds that target, decrease or inhibit the activity of the proteasome including, but not limited to, bortezomib.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and busulfan; and ALK inhibitors, which are compounds which target, decrease or inhibit anaplastic lymphoma kinase. Exemplary Flt-3 inhibitors include PKC412, midostaurin, a staurosporine derivative, SU11248 and MLN518.

Exemplary HSP90 inhibitors include compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing or inhibiting the activity of the platelet-derived growth factor-receptors (PDGFR), such as a compound which targets, decreases, or inhibits the activity of PDGFR, such as an N-phenyl-2-pyrimidine-amine derivatives, such as imatinib, SU101, SU6668 and GFB-111; b) a compound targeting, decreasing or inhibiting the activity of the fibroblast growth factor-receptors (FGFR); c) a compound targeting, decreasing or inhibiting the activity of the insulin-like growth factor receptor I (IGF-IR), such as a compound which targets, decreases, or inhibits the activity of IGF-IR; d) a compound targeting, decreasing or inhibiting the activity of the Trk receptor tyrosine kinase family, or ephrin B4 inhibitors; e) a compound targeting, decreasing or inhibiting the activity of the Axl receptor tyrosine kinase family; f) a compound targeting, decreasing or inhibiting the activity of the Ret receptor tyrosine kinase; g) a compound targeting, decreasing or inhibiting the activity of the Kit/SCFR receptor tyrosine kinase, such as imatinib; h) a compound targeting, decreasing or inhibiting the activity of the c-Kit receptor tyrosine kinases, such as imatinib; i) a compound targeting, decreasing or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol; BAY 43-9006, bryostatin 1, perifosine; ilmofosine; RO 318220 and RO 320432; GO 6976; ISIS 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) a compound targeting, decreasing or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing or inhibiting the activity of the c-Met receptor.

Exemplary compounds that target, decrease or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g. thalidomide and TNP-470.

Additional exemplary chemotherapeutic compounds, one or more of which may be used in combination with provided compounds, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugen; FLT-4 inhibitors, FLT-3 inhibitors, VEGFR-2 IgG1 antibody, RPI 4610, bevacizumab, porfimer sodium, anecortave, triamcinolone, hydrocortisone, 11-α-epihydrocotisol, cortexolone, 17α-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA or siRNA, or a miscellaneous compound or compound with other or unknown mechanism of action. For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and)Rebif®, glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

The above-mentioned compounds, one or more of which can be used in combination with a provided compound, can be prepared and administered as described in the art. Provided compounds can be administered alone or in combination with one or more other therapeutic compounds, possible combination therapy taking the form of fixed combinations or the administration of a provided compound and one or more other therapeutic compounds being staggered or given independently of one another, or the combined administration of fixed combinations and one or more other therapeutic compounds. Provided compounds can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a composition containing a provided compound, as part of a multiple dosage regimen. Alternatively, those agents may be part of a single dosage form, mixed together with a provided compound in a single composition. If administered as part of a multiple dosage regimen, the two active agents may be submitted simultaneously, sequentially or within a period of time from one another normally within five hours from one another.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses.

As used herein, the term "combination," "combined," and related terms refers to the simultaneous or sequential administration of therapeutic agents in accordance with this invention. For example, a provided compound may be administered with another therapeutic agent simultaneously or sequentially in separate unit dosage forms or together in a single unit dosage form. Accordingly, an embodiment of the invention provides a single unit dosage form comprising a provided compound, an additional therapeutic agent, and a pharmaceutically acceptable carrier, adjuvant, or vehicle for use in the methods of the invention.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this disclosure will be no more than the amount that would normally be administered in a composi tion comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a provided compound. Implantable devices coated with a compound of this invention are another embodiment of the present invention.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

In another aspect, the invention provides a method of method of synthesizing a compound of any formulae as described herein. Another embodiment is a method of making a compound of any of the formulae herein using any one, or combination of, reactions delineated herein. The method can include the use of one or more intermediates or chemical reagents delineated herein.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Scheme 1 depicts the synthesis Compounds 1, 2, 3 and 4 of the invention.

Scheme 1

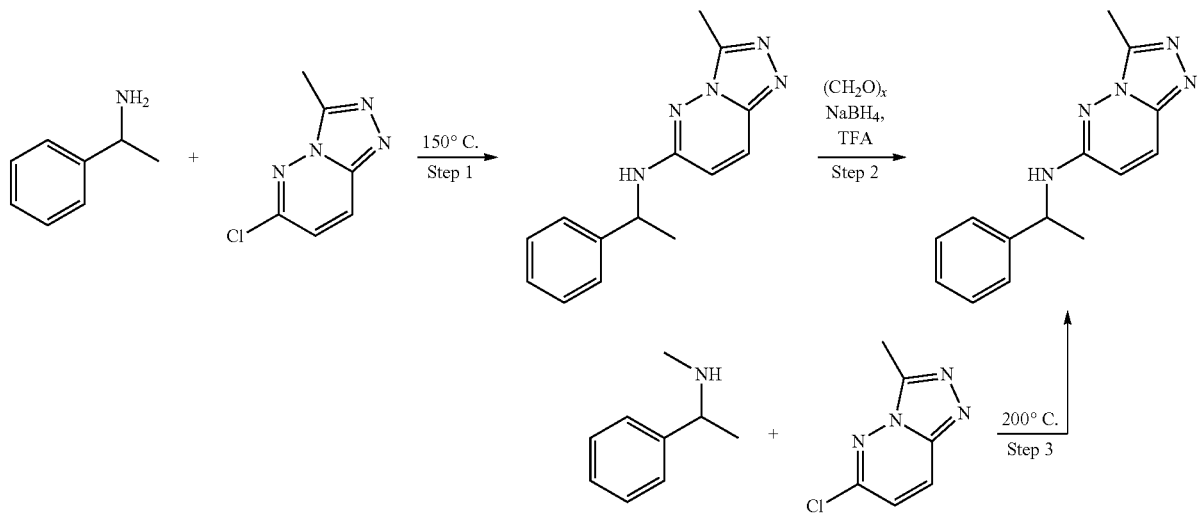

Example 1

Synthesis of N,3-dimethyl-N-(1-phenylethyl)-[1,2,4]triazolo[4,3-b]pyridazin-6-amine (Compound 1)

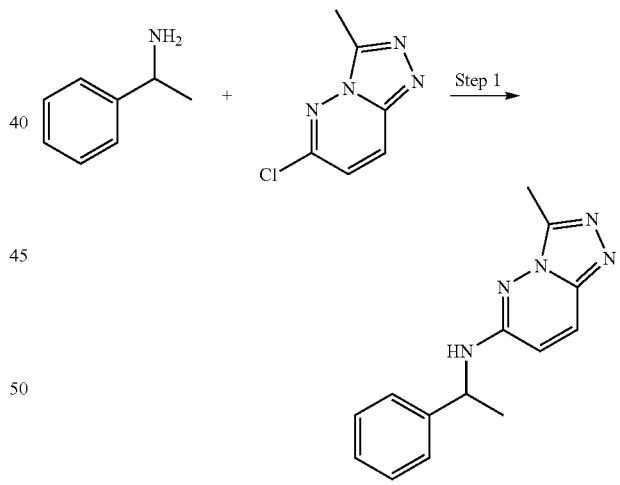

6-Chloro-3-methyl-[1,2,4]triazolo[4,3-b]pyridazine (200 mg, 1.186 mmol; commercially available or prepared according to patent WO2006/039325A2), rac-1-phenylethanamine (575 mg, 4.75 mmol; commercially available from Aldrich) and anhydrous NMP (1 mL) were charged into a microwave tube equipped with a magnetic stirbar (light brown solution). After the vessel was sealed, the mixture was heated at 150° C. for 15 min, followed by an extra 45 min using microwave irradiation. The reaction was then diluted with MeOH/H$_2$O (19:1), filtered, purified by reverse phase chromatography and lyophilized to give the rac-3-methyl-N-(1-phenylethyl)-[1,2,4]triazolo[4,3-b]pyridazin-6-amine (Compound 1) as a white solid (42 mg; 14% yield). $^1$H NMR (400 MHz, DMSO-d$_6$): δ 7.84 (d, J=9.8 Hz, 1H), 7.81 (d, J=7.1 Hz, 1H), 7.42 (d, J=7.8 Hz, 2H), 7.32 (t, J=7.5 Hz, 2H), 7.21 (t, J=7.3 Hz, 1H), 6.80 (d, J=9.8 Hz, 1H), 4.92 (dd, J=7.0, 7.0 Hz, 1H), 2.42 (s, 3H), 1.49 (d, J=6.9 Hz, 3H). LRMS [M+H]$^+$: 254 m/z.

Example 2

Synthesis of N,3-dimethyl-N-(1-phenylethyl)-[1,2,4]triazolo[4,3-b]pyridazin-6-amine (Compound 2)

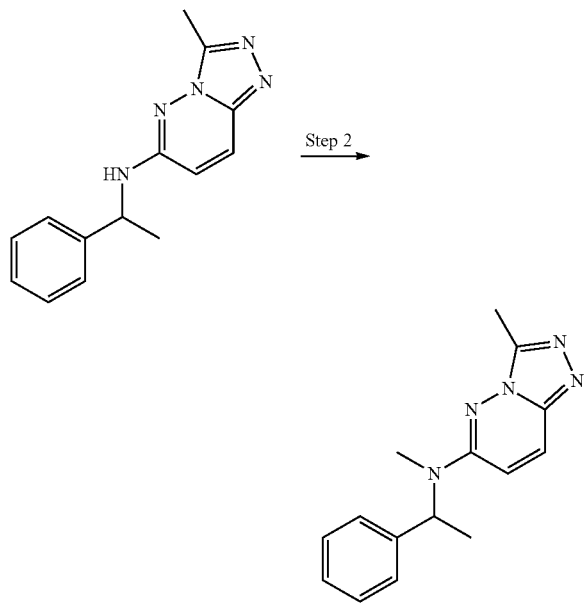

3-Methyl-N-(1-phenylethyl)-[1,2,4]triazolo[4,3-b]pyridazin-6-amine (100 mg, 0.395 mmol), paraformaldehyde (119 mg, 3.95 mmol), NaBH$_4$ (74.7 mg, 1.974 mmol) and anhydrous THF (5 mL) were charged into a disposable reaction tube equipped with a stirbar and a septum. TFA (2.5 mL) was slowly added at room temperature over 1 h and the reaction was stirred for an additional 18 h at room temperature. A 1M aqueous solution of NaOH was added until pH~12 and the product was extracted with CH$_2$Cl$_2$/MeOH (19:1) (4×25 mL). The organic layers were combined, dried over Na$_2$SO$_4$ and concentrated to dryness. The crude product was then diluted with MeOH/H$_2$O (19:1), filtered, purified by preparative HPLC (reverse phase) and lyophilized to give the N,3-dimethyl-N-(1-phenylethyl)-[1,2,4]triazolo[4,3-b]pyridazin-6-amine (Compound 2) as a white solid (6 mg; 6% yield). $^1$H NMR (400 MHz, DMSO-d$_6$): δ 7.98 (d, J=10.1 Hz, 1H), 7.22-7.39 (m, 6H), 5.68 (q, J=6.9 Hz, 1H), 2.81 (s, 3H), 2.52 (s, 3H), 1.56 (d, J=7.1 Hz, 3H). LRMS [M+H]$^+$: 268 m/z.

Example 3

Synthesis of (R)-N,3-dimethyl-N-(1-phenylethyl)-[1,2,4]triazolo[4,3-b]pyridazin-6-amine (Compound 4)

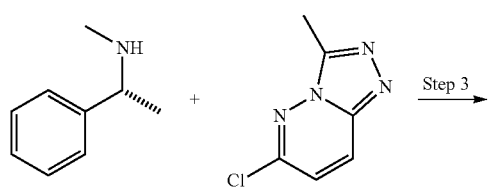

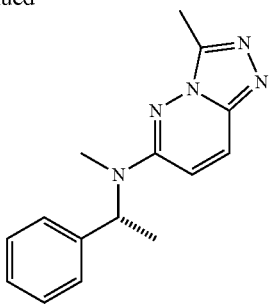

6-Chloro-3-methyl-[1,2,4]triazolo[4,3-b]pyridazine (150 mg, 0.890 mmol; commercially available or prepared according to patent WO2006/039325A2), (R)-N-methyl-1-phenylethanamine (481 mg, 3.56 mmol; available from Aldrich) and anhydrous NMP (1 mL) were charged into a microwave tube equipped with a magnetic stirbar. After the vessel was sealed, the mixture was heated at 200° C. for 60 min using microwave irradiation. The reaction was purified by normal phase (gradient of 0% to 20% MeOH in CH$_2$Cl$_2$ as eluent) and by reverse phase chromatography before being lyophilized to give the (R)-N,3-dimethyl-N-(1-phenylethyl)-[1,2,4]triazolo[4,3-b]pyridazin-6-amine (Compound 3) as an off-white solid (115 mg; 48% yield). $^1$H NMR (400 MHz, DMSO-d$_6$): δ 8.01 (d, J=10.1 Hz, 1H), 7.23-7.41 (m, 6H), 5.71 (q, J=6.8 Hz, 1H), 2.83 (s, 3H), 2.54 (s, 3H), 1.58 (d, J=7.1 Hz, 3H). LRMS [M+H]$^+$: 268 m/z.

Example 4

Synthesis of (S)-N,3-dimethyl-N-(1-phenylethyl)-[1,2,4]triazolo[4,3-b]pyridazin-6-amine (Compound 3)

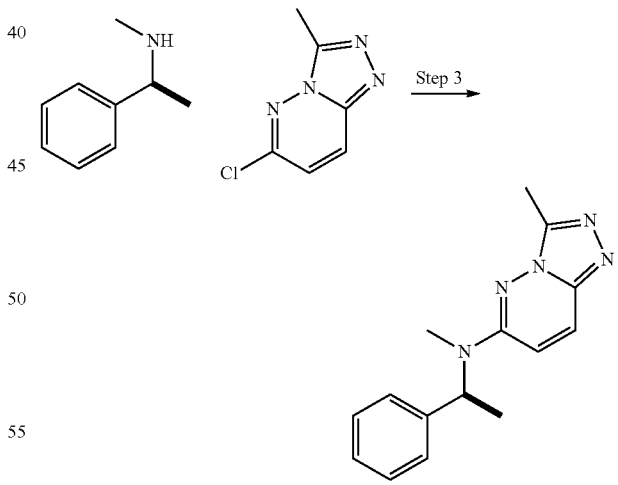

6-Chloro-3-methyl-[1,2,4]triazolo[4,3-b]pyridazine (120 mg, 0.712 mmol; commercially available or prepared according to patent WO2006/039325A2), (S)-N-methyl-1-phenylethanamine (385 mg, 2.85 mmol) and anhydrous NMP (1 mL) were charged into a microwave tube equipped with a magnetic stirbar. After the vessel was sealed, the mixture was heated at 200° C. for 60 min using microwave irradiation. The reaction was purified by normal phase chromatography (10% CH$_2$Cl$_2$ in hexane then a gradient of 0% to 20% MeOH in CH₂Cl₂) and by reverse phase chromatography before being lyophilized to give the (S)-N,3-dimethyl-N-(1-phenylethyl)-[1,2,4]triazolo[4,3-b]pyridazin-6-amine (Compound 3) as an off-white solid (69 mg; 36% yield). $^1$H NMR (400 MHz, DMSO-d$_6$): δ 8.01 (d, J=10.1 Hz, 1H), 7.25-7.39 (m, 6H), 5.71 (q, J=6.9 Hz, 1H), 2.84 (s, 3H), 2.54 (s, 3H), 1.58 (d, J=6.9 Hz, 3H). LRMS [M+H]$^+$: 268 m/z.

Example 5

Synthesis of (S)-1-ethyl-3-(3-methyl-6-(methyl(1-phenylethyl)amino)-[1,2,4]triazolo[4,3-b]pyridazin-8-yl)urea (Compound 5)

Compound 5 is produced according to Scheme 2:

Methyl 6-chloro-3-methyl-[1,2,4]triazolo[4,3-b]pyridazine-8-carboxylate: Thionyl chloride (2.0 mL) was added dropwise to a solution of 6-chloro-3-methyl-[1,2,4]triazolo[4,3-b]pyridazine-8-carboxylic acid (4.0 g, 18.5 mmol) in MeOH (100 mL) under cooling in an ice bath. The resulting mixture was stirred at 80° C. for more than 16 h. The reaction mixture was then cooled to room temperature and concentrated, and the crude product was purified by flash chromatography (silica gel, 1% to 10% MeOH in CH₂Cl₂) to give the methyl 6-chloro-3-methyl-[1,2,4]triazolo[4,3-b]pyridazine-8-carboxylate as a yellow solid (3.0 g, 72% yield). $^1$H NMR (300 MHz, CD₃OD): δ 7.92 (s, 1H), 4.07 (s, 3H), 2.79 (s, 3H). LRMS [M+H]$^+$: 226 m/z.

(S)-methyl 3-methyl-6-(methyl(1-phenylethyl)amino)-[1,2,4]triazolo[4,3-b]pyridazine-8-carboxylate. A solution of

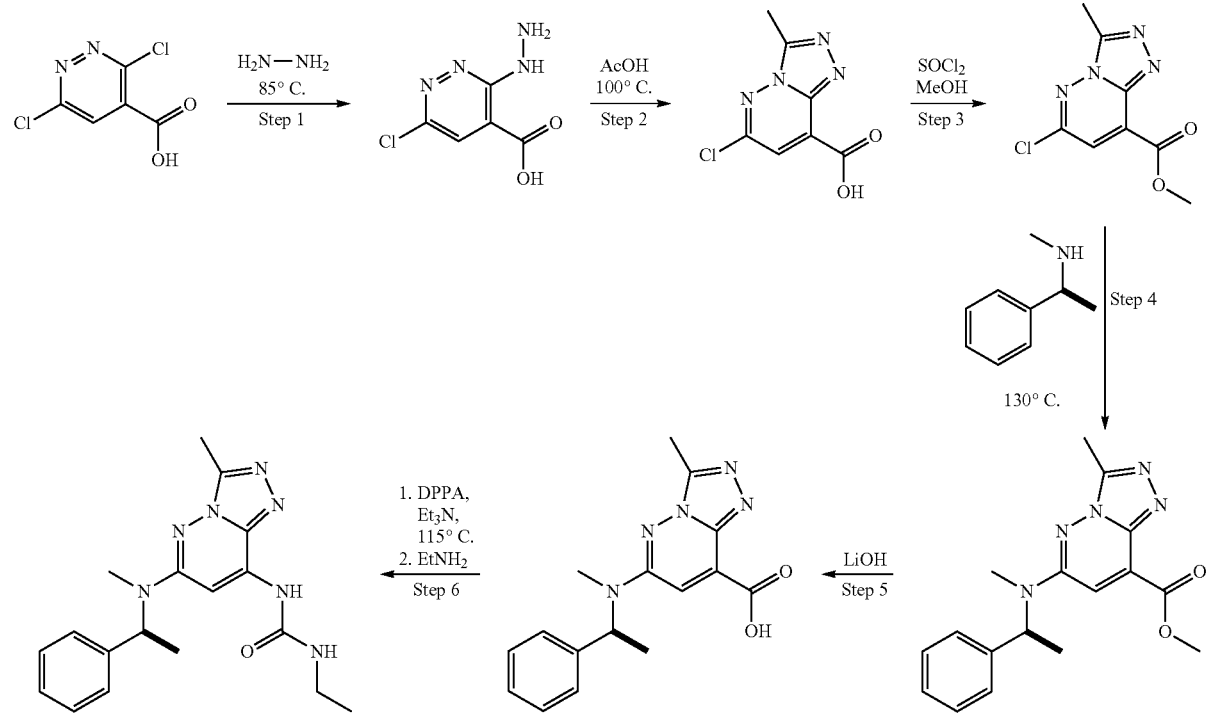

Scheme 2

6-chloro-3-hydrazinylpyridazine-4-carboxylic acid: To a solution of 3,6-dichloropyridazin-4-amine (5 g, 26 mmol; commercially available) in EtOH (200 mL) were added TEA (4 mL, 30 mmol) and hydrazine (5 mL, 80%). The reaction mixture was stirred at 85° C. for 3 h. TLC showed that SM was consumed and, after concentration in vacuo, the crude 6-chloro-3-hydrazinylpyridazine-4-carboxylic acid (4.8 g) was used directly without purification for the next step. LRMS [M+H]$^+$: 188 m/z.

6-chloro-3-methyl-[1,2,4]triazolo[4,3-b]pyridazine-8-carboxylic acid: A suspension of 6-chloro-3-hydrazinylpyridazine-4-carboxylic acid (4.8 g; crude product) in AcOH (100 mL) was heated at 100° C. for 3 h. The mixture was cooled to room temperature and concentrated to remove the solvent. Then the residue was washed by petroleum ether (50 mL) and recrystallized from MeOH to give the pure 6-chloro-3-methyl-[1,2,4]triazolo[4,3-b]pyridazine-8-carboxylic acid (4.0 g, 73% yield over two steps). $^1$H NMR (300 MHz, DMSO-d$_6$): δ 7.2 (s, 1H), 2.66 (s, 3H). LRMS [M+H]$^+$: 212 m/z.

methyl 6-chloro-3-methyl-[1,2,4]triazolo[4,3-b]pyridazine-8-carboxylate (2.0 g, 8.85 mmol) and (S)-N-methyl-1-phenylethanamine (2.39 g, 17.7 mmol; commercially available from Aldrich) in DMSO (20 mL) was heated at 130° C. in a microwave tube for 30 min. Water (100 mL) was added to the reaction mixture, and the product was extracted with EtOAc (3×100 mL). The combined EtOAc layers were concentrated and the residue was purified by flash chromatography (silica gel, 1% to 10% MeOH in CH₂Cl₂) to give the (S)-methyl 3-methyl-6-(methyl(1-phenylethyl)amino)-[1,2,4]triazolo[4,3-b]pyridazine-8-carboxylate (400 mg, 15% yield). LRMS [M+H]$^+$: 325 m/z.

(S)-3-methyl-6-(methyl(1-phenylethyl)amino)-[1,2,4]triazolo[4,3-b]pyridazine-8-carboxylic acid.

To a solution of (S)-methyl-3-methyl-6-(methyl(1-phenylethyl)amino)-[1,2,4]triazolo[4,3-b]pyridazine-8-carboxylate (400 mg, 1.22 mmol) in MeOH (15 mL) was added a 1M aqueous solution of LiOH (3.66 mL, 3.66 mmol). After 30 min, the organic solvent was removed under reduced pressure, and the pH of the aqueous layer was adjusted to pH=3 with 2N HCl, extracted with CH$_2$Cl$_2$ (3×50 mL). The combined organic layers were concentrated to give the (S)-3-methyl-6-(methyl(1-phenylethyl)amino)-[1,2,4]triazolo[4,3-b]pyridazine-8-carboxylic acid (325 mg, 85%). $^1$H NMR (300 MHz, CDCl$_3$): δ 7.95 (s, 1H), 7.29-7.42 (m, 5H), 5.83-5.85 (s, 1H), 2.98 (s, 3H), 2.70 (s, 3H), 1.70 (d, J=6.6 Hz, 3H), LRMS [M+H]$^+$: 311 m/z.

Compound 5

To a solution of (S)-N-3-dimethyl-N-(1-phenylethyl)-[1,2,4]triazolo[4,3-b]pyridazine-6,8-diamine (100 mg, 0.32 mmol) in anhydrous 1,4-dioxane (10 mL) were added DPPA (175 mg, 0.64 mmol) and triethylamine (100 µL, 0.64 mmol) under nitrogen atmosphere. The reaction mixture was stirred at 115° C. for 6 h, and cooled to 0° C. A 2M solution of ethyl amine in THF (1 mL, 2 mmol) was added at 0° C. before the reaction was heated to 60° C. for 16 h. The mixture was concentrated and extracted with CH$_2$Cl$_2$ (3×30 mL). The combined organic layers were washed with a saturated sodium bicarbonate solution (10 mL), dried with anhydrous Na$_2$SO$_4$ and concentrated. The crude product was first purified by preparative TLC (silica-gel, 7% MeOH in CH$_2$Cl$_2$), then by preparative HPLC to give the (S)-1-ethyl-3-(3-methyl-6-(methyl(1-phenylethyl)amino)-[1,2,4]triazolo[4,3-b]pyridazin-8-yl)urea (Compound 5) (5 mg, 4% yield). $^1$H NMR (300 MHz, DMSO-d$_6$): δ 9.45 (s, 1H), 7.75 (s, 1H), 7.27-7.35 (m, 5H), 7.12-7.18 (m, 1H), 5.62 (q, J=6.6 Hz, 1H), 3.12-3.16 (m, 2H), 2.78 (s, 3H), 2.53 (s, 3H), 1.57 (d, J=6.9 Hz, 3H), 1.07 (t, J=7.2 Hz, 3H). LRMS [M+H]$^+$: 353 m/z.

Example 6

Synthesis of 3-dimethyl-N$^6$-(1-phenylethyl)-[1,2,4]triazolo[4,3-b]pyridazine-6,8-diamine (Compound 6).

Compound 6 is synthesized according to Scheme 3 below.

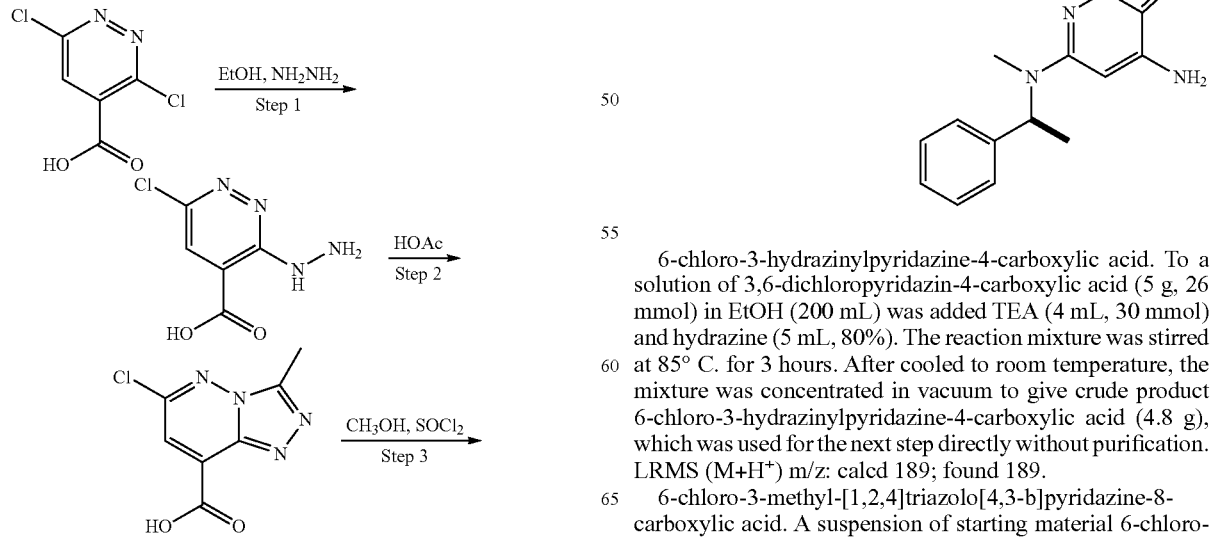

6-chloro-3-hydrazinylpyridazine-4-carboxylic acid. To a solution of 3,6-dichloropyridazin-4-carboxylic acid (5 g, 26 mmol) in EtOH (200 mL) was added TEA (4 mL, 30 mmol) and hydrazine (5 mL, 80%). The reaction mixture was stirred at 85° C. for 3 hours. After cooled to room temperature, the mixture was concentrated in vacuum to give crude product 6-chloro-3-hydrazinylpyridazine-4-carboxylic acid (4.8 g), which was used for the next step directly without purification. LRMS (M+H$^+$) m/z: calcd 189; found 189.

6-chloro-3-methyl-[1,2,4]triazolo[4,3-b]pyridazine-8-carboxylic acid. A suspension of starting material 6-chloro-3-hydrazinylpyridazine-4-carboxylic acid (4.80 g, 26 mmol)

in acetic acid (100 mL) was heated at 100° C. for 3 hours. The mixture was cooled to room temperature, concentrated in vacuum to give the crude product, which was washed by PE (50 mL) first, then recrystallized from MeOH to give product 6-chloro-3-methyl-[1,2,4]triazolo[4,3-b]pyridazine-8-carboxylic acid as a yellow solid (4.00 g, 72.5%). $^1$H NMR (300 MHz, DMSO) δ: 7.2 (s, 1H), 2.66 (s, 3H). LRMS (M+H$^+$) m/z: calcd 213; found 213.

Methyl 6-chloro-3-methyl-[1,2,4]triazolo[4,3-b]pyridazine-8-carboxylate

Thionyl chloride (2.0 mL) was added to a solution of product 6-chloro-3-methyl-[1,2,4]triazolo[4,3-b]pyridazine-8-carboxylic acid (4.0 g, 18.5 mmol) in MeOH dropwise under cooled ice-bath. The resulting mixture was stirred at 80° C. for 16 hours and then cooled to room temperature and concentrated in vacuum. The crude product was purified by flash column chromatography (silica-gel, PE: EA=3:1) to give product methyl 6-chloro-3-methyl-[1,2,4]triazolo[4,3-b]pyridazine-8-carboxylate as a yellow solid (3.0 g, 71.8%). $^1$H NMR (300 MHz, CD$_3$OD) δ: 7.92 (s, 1H), 4.07 (s, 3H), 2.79 (s, 3H). LRMS (M+H$^+$) m/z: calcd 227; found 227.

(S)-methyl 3-methyl-6-(methyl (1-phenylethyl) amino)-[1,2,4]triazolo[4,3-b]pyridazine-8-carboxylate A mixture of compound methyl 6-chloro-3-methyl-[1,2,4] triazolo[4,3-b]pyridazine-8-carboxylate (2.0 g, 8.85 mmol) and (S)-N-methyl-1-phenylethanamine (2.39 g, 17.7 mmol) in anhydrous DMSO (20 mL) was stirred for 30 min at 130° C. under microwave condition. After cooled to room temperature, the mixture was diluted with EA (100 mL) and washed with H$_2$O (100 mL*3). The organic layer was dried over Na$_2$SO$_4$, concentrated in vacuum and purified by flash column chromatography (silica-gel, DCM: MeOH=10:1) to give product (S)-methyl 3-methyl-6-(methyl (1-phenylethyl) amino)-[1,2,4]triazolo[4,3-b]pyridazine-8-carboxylate as a yellow oil (400 mg, 14.5%). LRMS (M+H$^+$) m/z: calcd 326; found 326.

(S)-3-methyl-6-(methyl(1-phenylethyl)amino)[1,2,4]triazolo[4,3-b]pyridazine-8-carboxylic acid A mixture of compound (S)-methyl 3-methyl-6-(methyl (1-phenylethyl) amino)-[1,2,4]triazolo[4,3-b]pyridazine-8-carboxylate (400 mg, 1.22 mmol) and LiOH (88 mg, 3.66 mmol) in MeOH (15 mL) was stirred at room temperature for 0.5 h and then concentrated in vacuum. The residue was dissolved with DCM (100 mL), adjusted pH to 3 with 2 N aq. HCl and washed with brine (20 mL). The organic layer was evaporated in vacuum to give product (S)-3-methyl-6-(methyl(1-phenylethyl)amino)-[1,2,4]triazolo[4,3-b]pyridazine-8-carboxylic acid as a yellow solid (330 mg, 85%). $^1$H NMR (300 MHz, CDCl$_3$) δ: 7.95 (s, 1H), 7.29~7.42 (m, 5H), 5.83~5.85 (s, 1H), 2.98 (s, 3H), 2.70 (s, 3H), 1.70 (d, 3H, J=6.6 Hz). LRMS (M+H$^+$) m/z: calcd 312; found 312.

(S)-tert-butyl 3-methyl-6-(methyl(1-phenylethyl) amino)-[1,2,4]triazolo[4,3-b]pyridazin-8-ylcarbamate A mixture of DPPA (264 mg, 0.96 mmol), t-BuOH (1.0 mL), TEA (0.96 mmol), (S)-3-methyl-6-(methyl(1-phenylethyl)amino)-[1,2,4]triazolo[4,3-b]pyridazine-8-carboxylic acid (200 mg, 0.64 mmol) in anhydrous 1,4-dioxane (10 mL) was heated to reflux and stirred for overnight. The mixture was quenched with water (40 mL) and extracted with EA (30 mL*3). The combined organic layers were washed with brine (50 mL), dried over Na$_2$SO$_4$ and concentrated in vacuum. The residue was purified by flash column chromatography (silica-gel, DCM: MeOH=10:1) to give product (S)-tert-butyl3-methyl-6-(methyl(1-phenylethyl)amino)-[1,2,4]triazolo[4,3-b] pyridazin-8-ylcarbamate as a yellow oil (60 mg, 24.5%). $^1$H NMR (300 MHz, CDCl$_3$) δ: 7.55 (s, 1H), 7.29~7.34 (m, 5H), 5.81~5.83 (s, 1H), 2.81 (s, 3H), 2.66 (s, 3H), 1.61 (d, 3H, J=6.9 Hz), 1.54 (s, 9H). LRMS (M+H$^+$) m/z: calcd 383; found 383.

(S)-N$^6$, 3-dimethyl-N$^6$-(1-phenylethyl)-[1,2,4]triazolo[4,3-b]pyridazine-6,8-diamine (Compound 6)

To a solution of compound (S)-tert-butyl 3-methyl-6-(methyl(1-phenylethyl)amino)-[1,2,4]triazolo[4,3-b]pyridazin-8-ylcarbamate (55 mg) in THF (10 mL) was added 6 N HCl (2 mL) dropwise under ice bath and then stirred at room temperature for 2 hrs. The mixture was quenched by saturated aqueous sodium bicarbonate solution (30 mL) and extracted with EA (20 mL×3). The combined organic layers were dried over Na$_2$SO$_4$, concentrated in vacuum to give product (S)-N$^6$, 3-dimethyl-N$^6$-(1-phenylethyl)-[1,2,4]triazolo[4,3-b]pyridazine-6,8-diamine (Compound 6) as a yellow solid (30 mg, 73.9%). $^1$H NMR (300 MHz, CD$_3$OD) δ: 7.22~7.25 (m, 4H), 7.15~7.18 (m, 1H), 6.30 (s, 12H), 5.69~5.72 (q, 1H), 2.79 (s, 3H), 2.68 (s, 3H),1.53 (d, 3H, J=4.8 Hz). LRMS (M+H$^+$) m/z: calcd 283; found 283.

Example 7

Synthesis of (S)-3-methyl-6-(methyl(1-phenylethyl) amino)-[1,2,4]triazolo[4,3-b]pyridazine-8-carboxamide (Compound 7)

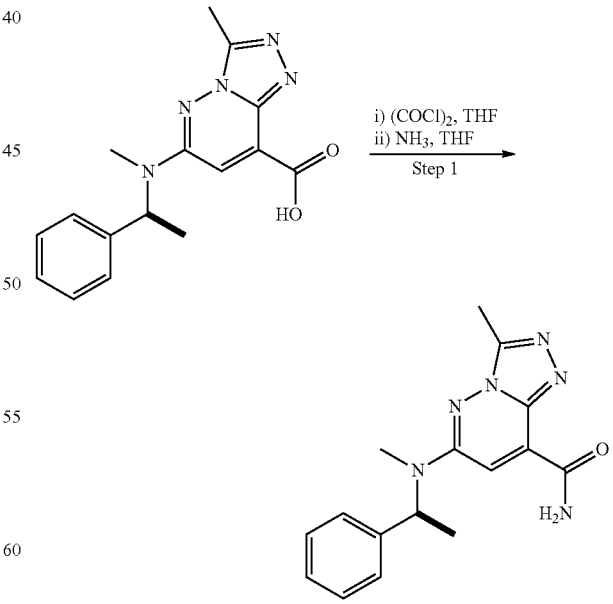

To a solution of compound (S)-3-methyl-6-(methyl(1-phenylethyl)amino)-[1,2,4]triazolo[4,3-b]pyridazine-8-carboxylic acid (200 mg, 0.64 mmol) in anhydrous THF (10 mL) was added oxalyl chloride (0.3 mL) dropwise. The reaction mixture was stirred at room temperature for 2 hrs, then 2N NH₃/THF (1 mL) solution was added, and stirred for another 2 hrs. The mixture was concentrated in vacuum and the residue was purified by flash column chromatography (silica-gel, DCM: MeOH=20:1) to give product (S)-3-methyl-6-(methyl (1-phenylethyl)amino)-[1,2,4]triazolo[4,3-b]pyridazine-8-carboxamide (Compound 7) as a yellow solid (180 mg, 90%). ¹H NMR (300 MHz, DMSO) δ 8.66 (s, 1H), 8.40 (s, 1H), 7.66 (s, 1H), 7.26~7.36 (m, 5H), 5.71~5.74 (q, 1H), 2.90 (s, 3H), 2.59 (s, 3H), 1.61 (d, J=6.9 Hz, 3H). LRMS (M+H⁺) calcd. 310; found 310.

Example 8

Synthesis of (S)-1,1-dimethyl-3-(3-methyl-6-(methyl (1-phenylethyl)amino)-[1,2,4]triazolo[4,3-b]pyridazin-8-yl)urea (Compound 8)

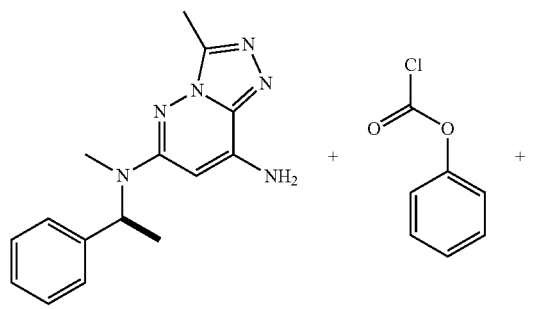

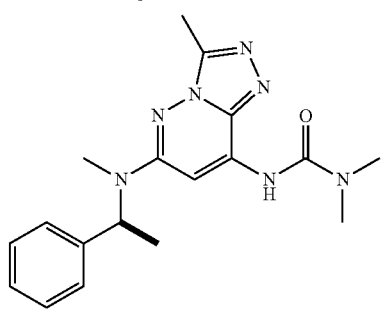

To a solution of compound (S)-N⁶, 3-dimethyl-N⁶-(1-phenylethyl)-[1,2,4]triazolo[4,3-b]pyridazine-6,8-diamine (50 mg, 0.17 mmol) in DCM (10 mL) was added phenyl carbonochloridate (30 mg, 0.19 mmol) dropwise at 0° C. The reaction mixture was stirred at room temperature for 1 h and then the solution of dimethylamine in THF (0.3 mL, 1 N) was added, and the mixture was stirred at room temperature for 2 h. The reaction mixture was diluted with water (15 mL) and extracted with EA (20 mL*3). The combined organic layers were dried over Na₂SO₄, concentrated in vacuum. The residue was purified by prep-TLC (DCM: MeOH=20:1) to give product (S)-1,1-dimethyl-3-(3-methyl-6-(methyl(1-phenylethyl)amino)-[1,2,4]triazolo[4,3-b]pyridazin-8-yl)urea (Compound 8) as a yellow solid (10 mg, 16.7%). ¹H NMR (300 MHz, CDCl₃) δ 7.96 (s, 1H), 7.80 (s, 1H), 7.34-7.32 (m, 5H), 3.12 (s, 6H), 2.80 (s, 3H), 2.65 (s, 3H), 1.60 (d, 3H); LRMS (M+H⁺) m/z: calcd 353.20; found 353.

Example 9

Synthesis of (S)-6-(methyl(1-phenylethyl)amino)-[1,2,4]triazolo[4,3-b]pyridazine-3-carbonitrile (Compound 9)

Compound 9 was synthesized according to Scheme 4, below.

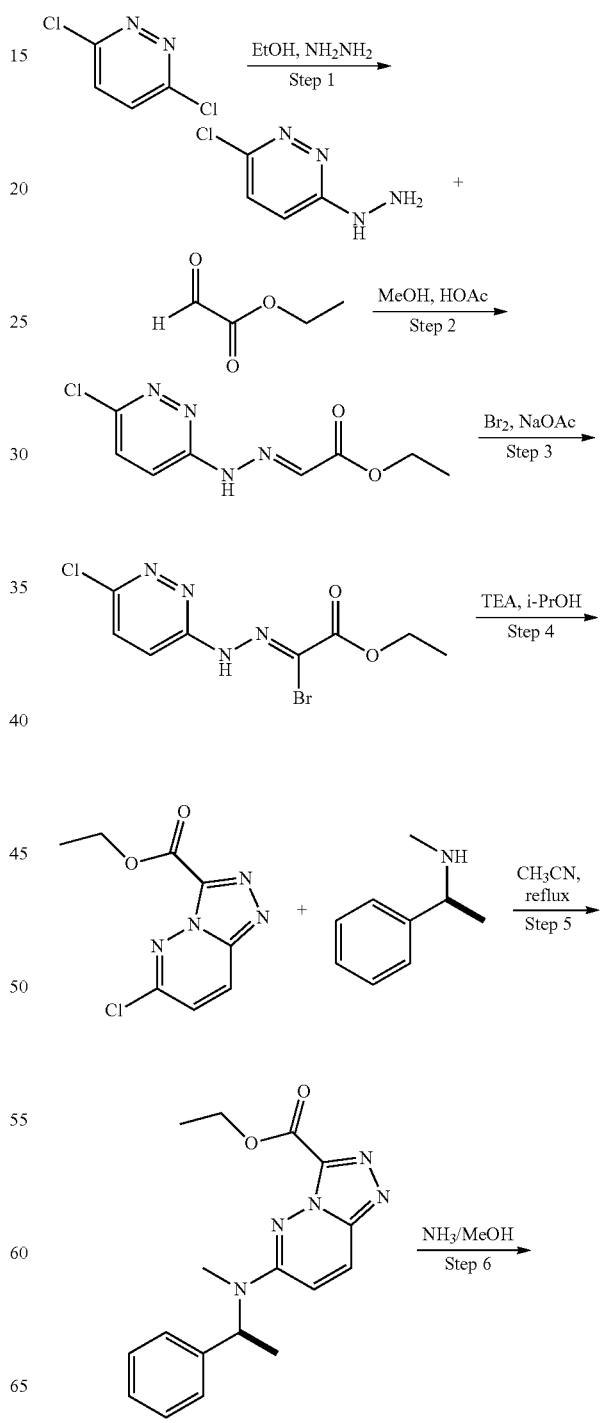

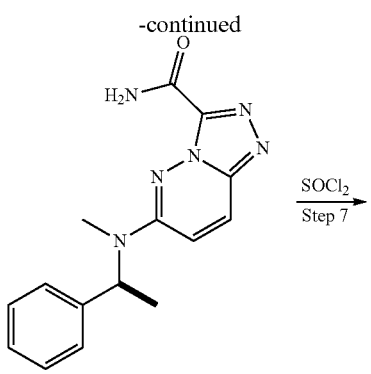

3-chloro-6-hydrazinylpyridazine. A mixture of 3,6-dichloropyridazine (20 g, 0.135 mol) and 20 mL of 80% hydrazine hydrate in 40 mL of ethanol was refluxed for 1 h. The reaction mixture was evaporated to dryness and the residue was recrystallized from benzene to give 3-chloro-6-hydrazinylpyridazine as a yellow solid (19 g, 96%). LRMS (M+H⁺) m/z: calcd 145.03; found 145.

1-ethoxycarbonylmethylene-2-(6-chloro-3-pyridazinyl) hydrazine

A mixture of compound 3-chloro-6-hydrazinylpyridazine (8.85 g, 0.061 mol) and ethyl glyoxalate (6.16 g, 0.061 mol) in 50 mL of methanol containing about 30% acetic acid was stirred at room temperature for 2 h. The yielded solid was collected by filtration and washed with methanol to give product 1-ethoxycarbonylmethylene-2-(6-chloro-3-pyridazinyl) hydrazine as a white solid (9.5 g, 68%). LRMS (M+H⁺) m/z: calcd 229.03; found 229. $^1$H NMR (300 MHz, CDCl$_3$): δ 12.40 (s, 1H), 7.80-7.31 (d, J=9.6 Hz, 1H), 7.60-7.56 (d, J=9.3 Hz, 1H), 7.50 (s, 1H), 4.25-4.23 (q, 2H), 1.31-1.26 (t, 3H).

Ethyl 2-bromo-2-(2-(6-chloropyridazin-3-yl)hydrazono)acetate

To a solution of compound 1-ethoxycarbonylmethylene-2-(6-chloro-3-pyridazinyl) hydrazine (11.4 g, 0.05 mol) and sodium acetate (11 g, 0.05 mol) in 50 mL of HOAc, bromine (8 g, 0.05 mol) in HOAc was added dropwise during 20 min. Stirring was continued for 3 h, the mixture was diluted with water (1 L), the precipitated crystals were filtered off, washed with water to give product ethyl 2-bromo-2-(2-(6-chloropyridazin-3-yl)hydrazono)acetate as a yellow solid (10 g, 66%). $^1$H NMR (300 MHz, d$_6$-DMSO): δ 9.33 (br, 1H), 7.69-7.66 (d, J=9.0 Hz, 1H), 7.50-7.47 (d, J=9.0 Hz, 1H), 4.44-4.37 (q, 2H), 1.43-1.39 (t, 3H).

Ethyl 6-chloro-[1,2,4]triazolo[4,3-b]pyridazine-3-carboxylate

A mixture of compound ethyl 2-bromo-2-(2-(6-chloropyridazin-3-yl)hydrazono)acetate (1.25 g, 4 mmol) in 10 mL of isopropanol with 0.5 mL of triethylamine was refluxed for 1 h. The solution was evaporated and the residue was washed thoroughly with water to give product ethyl 6-chloro-[1,2,4]triazolo[4,3-b]pyridazine-3-carboxylate as a yellow solid (0.8 g, 67%). LRMS (M+H⁺) m/z: calcd 227.03; found 227. $^1$H NMR (300 MHz, CDCl$_3$): δ 8.25-8.22 (d, J=9.6 Hz, 1H), 7.34-7.31 (d, J=9.6 Hz, 1H), 4.64-4.56 (q, 2H), 1.53-1.49 (t, 3H).

(S)-ethyl 6-(methyl(1-phenylethyl)amino)-[1,2,4]triazolo[4,3-b]pyridazine-3-carboxylate A solution of ethyl 6-chloro-[1,2,4]triazolo[4,3-b]pyridazine-3-carboxylate (1.5 g, 6.6 mmol) and (S)-N-methyl-1-phenylethanamine (3.6 g, 26.4 mmol) in 20 mL of CH$_3$CN was heated to reflux and stirred for 36 h. When cooled to room temperature, the reaction mixture was concentrated in vacuum, and the residue was purified by flash chromatography eluting with DCM/EA=5:1 to give product (S)-ethyl 6-(methyl(1-phenylethyl)amino)-[1,2,4]triazolo[4,3-b]pyridazine-3-carboxylate as a yellow oil (0.7 g, 32%). LRMS (M+H⁺) m/z: calcd 326.16; found 326. $^1$H NMR (300 MHz, CDCl$_3$): δ 8.02-7.99 (d, J=9 Hz, 1H), 7.36-7.26 (m, 5H), 7.09-7.06 (d, J=9 Hz, 1H), 5.82-5.75 (q, 1H), 4.57-4.50 (q, 2H), 2.94 (s, 3H), 1.68-1.65 (d, 3H), 1.48-1.44 (t, 3H).

(S)-6-(methyl(1-phenylethyl)amino)-[1,2,4]triazolo[4,3-b]pyridazine-3-carboxamide A solution of compound (S)-ethyl 6-(methyl(1-phenylethyl)amino)-[1,2,4]triazolo[4,3-b]pyridazine-3-carboxylate (0.5 g, 1.5 mmol) in 5 mL of methanolic ammonia (7N) was stirred for 0.5 h at room temperature. The mixture was concentrated in vacuum to give product (S)-6-(methyl(1-phenylethyl)amino)-[1,2,4]triazolo[4,3-b]pyridazine-3-carboxamide as a yellow solid (0.42 g, 92%). LRMS (M+H⁺) m/z: calcd 297.15; found 297. $^1$H NMR (300 MHz, CDCl$_3$): δ 8.11 (br, 1H), 8.05-8.02 (d, J=9 Hz, 1H), 7.40-7.29 (m, 5H), 7.13-7.10 (d, J=9 Hz, 1H), 6.47 (br, 1H), 5.57-5.55 (q, 1H), 2.97 (s, 3H), 1.71-1.69 (d, 3H).

(S)-6-(methyl(1-phenylethyl)amino)-[1,2,4]triazolo[4,3-b]pyridazine-3-carbonitrile (Compound 9)

To a solution of compound (S)-6-(methyl(1-phenylethyl)amino)-[1,2,4]triazolo[4,3-b]pyridazine-3-carboxamide (0.1 g, 0.34 mmol) in 2 mL of DMF, 1 mL of SOCl$_2$ was added dropwise at 0-5° C., the reaction mixture was stirred for 5 h at room temperature. The mixture was poured onto ice (20 mL) and the mixture was neutralized with NaHCO$_3$. DCM (50 mL) was added; the separated organic layer was dried over anhydrous Na$_2$SO$_4$, and concentrated in vacuum. The residue was purified by flash chromatography eluting with PE/EA=5:1 to give product (S)-6-(methyl(1-phenylethyl)amino)-[1,2,4]triazolo[4,3-b]pyridazine-3-carbonitrile as a yellow solid (Compound 9) (60 mg, 64%). LRMS (M+H⁺) m/z: calcd 279.43; found 279. $^1$H NMR (300 MHz, CDCl$_3$): δ 7.98-7.94 (d, J=12 Hz, 1H), 7.35-7.30 (m, 5H), 7.11-7.08 (d, J=9 Hz, 1H), 5.77-5.75 (q, 1H), 2.94 (s, 3H), 1.69-1.66 (d, 3H).

Example 10

Synthesis of 3-methyl-6-(2-phenylpyrrolidin-1-yl)-[1,2,4]-triazolo[4,3-b]pyridazine (Compound 10)

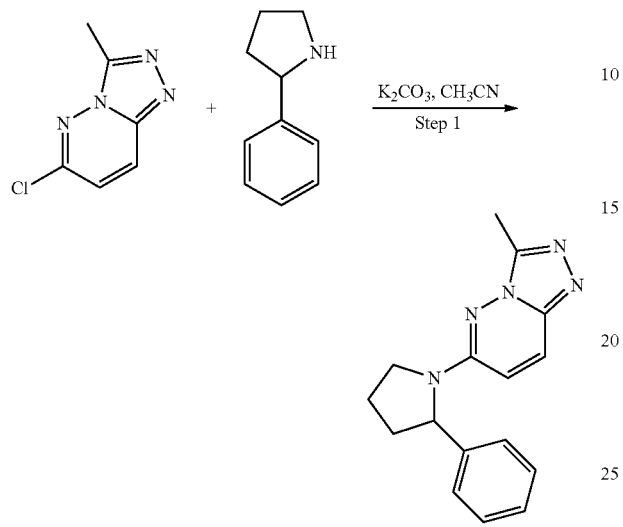

A mixture of 6-chloro-3-methyl-[1,2,4]triazolo[4,3-b]pyridazine (200 mg, 1.19 mol), 2-phenylpyrrolidine (200 mg, 1.36 mmol) and K₂CO₃ (350 mg, 2.5 mmol) in acetonitrile (20 mL) was heated at 100° C. under microwave and stirred for 30 mins. After cooled to room temperature, the reaction mixture was diluted with water (20 mL) and extracted with ethyl acetate (20 mL*3). The combined organic layer was washed with brine (10 mL), dried over Na₂SO₄ and concentrated in vacuum. The residue was purified by prep-TLC (silica-gel, DCM: MeOH=20:1) to give product 3-methyl-6-(2-phenylpyrrolidin-1-yl)-[1,2,4]triazolo[4,3-b]pyridazine (Compound 10) as a white solid (30 mg, 12%). ¹H NMR (300 MHz, CD₃OD) δ 7.73-7.77 (d, 1H, J=10.2 Hz), 7.22-7.34 (m, 5H), 6.84-6.87 (d, 1H, J=10.2 Hz), 5.14-5.18 (m, 1H), 3.92-3.98 (m, 1H), 3.71-3.81 (m, 1H), 2.57 (s, 3H), 2.50-2.54 (M, 1H), 2.03-2.13 (m, 3H); LRMS (M+H⁺) m/z: calcd 279.15; found 279.

Additional compounds of the invention were made using similar procedures and the appropriate intermediates and reagents. Compounds 11-14 were made in an analagous manner to Compound 5.

Example 11

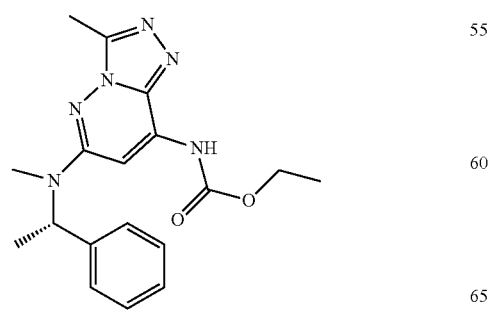

Compound 11: ¹H NMR (300 MHz, CDCl₃): δ 8.51 (s, 1H), 7.65 (s, 1H), 7.38-7.26 (m, 5H), 5.79 (m, 1H), 4.29 (m, 2H), 2.83 (s, 3H), 2.66 (s, 3H), 1.62 (d, J=6.9 Hz, 3H), 1.35 (t, J=7.2 Hz, 3H).

Example 12

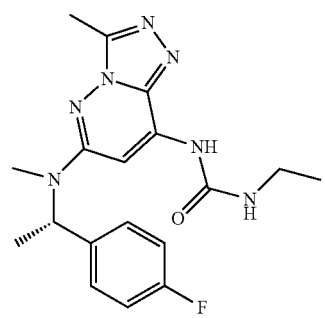 [SMILES: CCNC(=O)Nc1cc(N(C)[C@@H](C)c2ccc(F)cc2)nn2c(C)nnc12]

Compound 12: ¹H NMR (300 MHz, CDCl₃): δ 8.05 (s, 1H), 7.33-7.27 (m, 2H), 7.04 (m, 2H), 5.85-5.80 (m, 1H), 3.42-3.38 (m, 2H), 2.82 (s, 3H), 2.68 (s, 3H), 1.61 (d, J=6.9 Hz, 3H), 1.28 (t, J=6.9 Hz, 3H).

Example 13

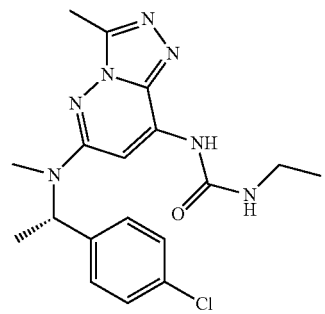 [SMILES: CCNC(=O)Nc1cc(N(C)[C@@H](C)c2ccc(Cl)cc2)nn2c(C)nnc12]

Compound 13: ¹H NMR (300 MHz, CDCl₃): δ 8.03 (s, 1H), 7.32-7.26 (m, 4H), 5.83-5.76 (m, 1H), 3.43-3.34 (m, 2H), 2.80 (s, 3H), 2.65 (s, 3H), 1.59 (d, J=6.9 Hz, 3H), 1.27 (t, J=7.2 Hz, 3H).

Example 14

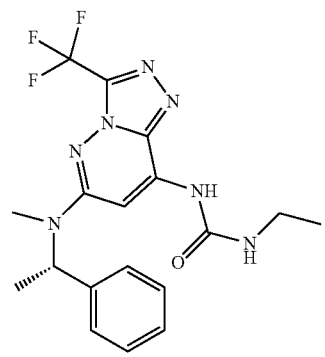 [SMILES: CCNC(=O)Nc1cc(N(C)[C@@H](C)c2ccccc2)nn2c(C(F)(F)F)nnc12]

Compound 14: $^1$H NMR (CDCl$_3$, 300 MHz) δ 9.69 (br s, 1H), 8.46 (br s, 1H), 8.17 (s, 1H), 7.26-7.38 (m, 5H), 7.12-7.18 (m, 1H), 5.82 (q, J=6.9 Hz, 1H), 3.35-3.44 (m, 2H), 2.86 (s, 3H), 1.63 (d, J=6.9 Hz, 3H), 1.25 (t, J=7.2 Hz, 3H).

Biological Assays

A. IC50 Measurements for Inhibitors Using BRD4 AlphaLisa Binding Assay

His/Flag epitope tagged BRD4 BD1$_{42-168}$ was cloned, expressed and purified to homogeneity. BRD4 binding and inhibition was assessed by monitoring the engagement of biotinylated H4-tetraacetyl peptide (Millipore #12-379) with the target using the AlphaLisa technology (Perkin-Elmer). Specifically, in a 384 well ProxiPlate BRD4(BD1) (30 nM final) was combined with peptide (200 nM final) in 40 mM HEPES (pH 7.0), 40 mM NaCl, 1 mM DTT, 0.01% (w/v) BSA, and 0.008% (w/v) Brij-35 either in the presence of DMSO (final 1.2% DMSO) or compound dilution series in DMSO. After 20 minute incubation at room temperature Alpha streptavidin donor beads and AlphaLisa anti-Flag acceptor beads were added to a final concentration of 10 ug/mL each. After three hours equilibration plates were read on an Envision instrument and IC$_{50}$s calculated using a four parameter non-linear curve fit.

B. cMyc RNA quantification assay (QuantiGene® Assay)

MV4:11 (AML) or Raji (Burkitt lymphoma) cells were seeded in a 96-well plate and incubated in the presence of various concentrations of compounds for 4 h. Relative mRNA levels were quantitated by using QuantiGene 2.0 assay (Affymetrix) according to the manufacturer's recommendation. Signals were detected by using an Envision plate reader (Perkin-Elmer). Biological duplicates were averaged and normalized to vehicle (DMSO) control to calculate percent MYC mRNA levels.

C. Cell-Based IL-6 Quantification Assay (ELISA, Mesoscale Assay):

100,000 THP-1 cells were seeded in RPMI1640-10% FBS in 96-well plates. LPS (E. Coli Invitrogen) in RPMI-10% FBS at a final concentration of 4 μg/mL was added to the wells and the cells are then incubated in the presence of various concentrations of compounds for 16 h. Plates are spun (2 rpm, 5 min), an aliquot of 25 uL supernatant is transferred in to an ELISA plate (Mesoscale technology, MSD) and the detection of IL-6 is performed using manufacturer's instructions. The amount of cells in each well is assessed using CellTiter-Glo® (Promega). The ratio of ELISA value/CellTiter-Glo value is used to calculate the percent of inhibition of IL-6 secretion.

The results of these assays are set forth in Table 2, below.

TABLE 2

Activity of Exemplary Compounds of the Invention

| Compound No. | BRD4 IC$_{50}$ | IL-6 | cMYc mRNA (Raji) | cMYc mRNA (MV4-11) |
|---|---|---|---|---|
| 1 | C | C | NT | C |
| 2 | B | C | NT | NT |
| 3 | A | C | NT | NT |
| 4 | C | NT | NT | NT |
| 5 | A | A | A | NT |
| 6 | A | A | NT | NT |
| 7 | C | C | NT | NT |
| 8 | A | B | C | NT |
| 9 | C | C | NT | C |
| 10 | C | NT | NT | NT |
| 11 | A | A | A | NT |
| 12 | A | A | NT | A |
| 13 | A | A | NT | A |
| 14 | A | A | NT | A |

In Table 2, "A" represents a value under 0.50 μM; "B" a value between 0.50 μM and 1 μM; and "C" a value greater than 1 μM. "NT" represents that the compound was not tested in the indicated assay.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

We claim:

1. A compound of formula II:

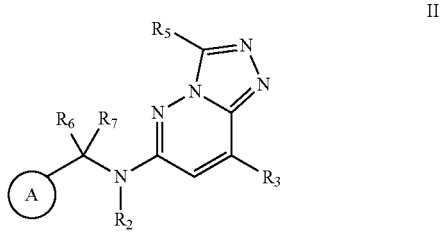

or a pharmaceutically acceptable salt thereof, wherein:

ring A is optionally substituted aryl or optionally substituted heteroaryl;

$R_6$ is optionally substituted alkyl;

$R_7$ is H or optionally substituted alkyl; or $R_6$ and $R_7$, together with the atom to which each is attached, forms a carbocyclic or heterocyclic, each of which is optionally substituted;

$R_2$ is H, optionally substituted alkyl, optionally substituted aryl, optionally substituted aralkyl, optionally substituted cycloalkyl, optionally substituted heteroaryl, optionally substituted heterocycloalkyl, haloalkyl, or —(CH$_2$)$_p$R$_x$; or $R_2$ and $R_6$, together with the atoms to which each is attached, form a heterocyclic or heteroaryl ring, each of which is optionally substituted;

p is 1, 2, 3, 4, 5, or 6;

$R_3$ is H, OR$_A$, NR$_A$R$_B$, N(R$_A$)S(O)$_q$R$_A$R$_B$, N(R$_A$)C(O)R$_B$, N(R$_A$)C(O)NR$_A$R$_B$, N(R$_A$)C(O)OR$_A$, N(R$_A$)C(S) NR$_A$R$_B$, or OC(O)R$_A$;

each $R_A$ is independently optionally substituted alkyl, optionally substituted alkenyl or optionally substituted alkynyl, each containing 0, 1, 2, or 3 heteroatoms selected from O,S, or N; optionally substituted aryl; optionally substituted heteroaryl; optionally substituted heterocyclic; optionally substituted carbocyclic; or hydrogen;

each $R_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or $R_A$ and $R_B$, together with the atoms to which each is attached, can form a heterocycloalkyl or a heteroaryl; each of which is optionally substituted;

$R_5$ is Me, Et, Pr, —CH$_2$CF$_3$, —CF$_3$, CF$_2$CF$_3$, CN, F, Cl, Br, or I;

$R_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R''), —C(O)R, —C(S)R, —CO$_2$R, —C(O)N(R')(R''), —C(O)SR, —C(O)C(O)R, —C(O)CH$_2$C(O)R, —C(S)N(R')(R''), —C(S)OR, —S(O)R, —SO$_2$R, —SO$_2$N(R')(R''), —N(R')C(O)R, —N(R')C(O)N(R')(R''), —N(R')C(S)N(R')(R''), —N(R')SO$_2$R, —N(R')SO$_2$N(R')(R''), —N(R')N(R')(R''), —N(R')C(=N(R'))N(R')(R''), —C=NN(R')(R''), —C=NOR, —C(=N(R'))N(R')(R''), —OC(O)R, —OC(O)N(R')(R'');

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; and each R'' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; or R' and R'', together with the atoms to which each is attached, can form a cycloalkyl, a heterocycloalkyl, an aryl, or a heteroaryl; each of which is optionally substituted.

2. The compound according to claim 1, wherein ring A is phenyl, napthyl, pyridyl, pyrimidinyl, pyrazinyl, pyridazinyl, furyl, thiophenyl, pyrrolo, isoxazolyl, or isothiazolyl; each of which is optionally substituted.

3. The compound according to claim 1, wherein $R_6$ is methyl, ethyl, propyl, butyl, pentyl, or hexyl; each of which is optionally substituted.

4. The compound according to claim 1, wherein $R_2$ is H, methyl, ethyl, propyl, butylpentyl, hexyl, phenyl, or napthyl; each of which is optionally substituted.

5. The compound according to claim 1, wherein $R_3$ is H, OR$_A$, NR$_A$R$_B$, N(R$_A$)C(O)R$_B$, N(R$_A$)C(O)OR$_A$, or OC(O)R$_A$.

6. The compound according to claim 1, having the structural formula IV:

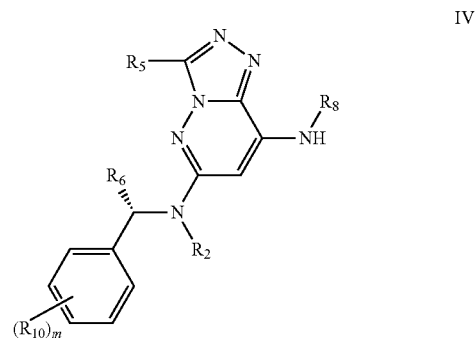

IV or a pharmaceutically acceptable salt thereof, wherein:
$R_2$ is optionally substituted alkyl;
$R_6$ is optionally substituted alkyl;
$R_8$ is selected from hydrogen, —C(O)NR$_A$R$_B$ and —C(O)OR$_A$, wherein each of R$_A$ and R$_B$ is independently selected from hydrogen or alkyl;
each $R_{10}$ is an independently selected substituent;
p is 1, 2, 3, 4, 5, or 6; and
m is 0, 1, 2 or 3.

7. The compound according to claim 6, wherein $R_2$ is methyl.

8. The compound according to claim 6, wherein $R_5$ is methyl.

9. The compound according to claim 6, wherein $R_6$ is methyl.

10. The compound according to claim 6, wherein $R_8$ is selected from hydrogen, —C(O)—N(CH$_3$)$_2$, —C(O)—NH—CH$_2$CH$_3$, and —C(O)—O—CH$_2$CH$_3$.

11. The compound according to claim 6, wherein m is 0 or 1; and when m is 1, $R_{10}$ is a para substituent selected from fluoro and chloro.

12. A compound selected from:

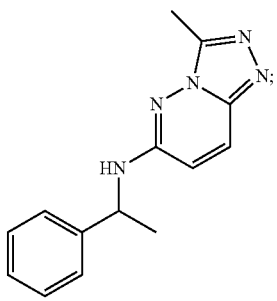

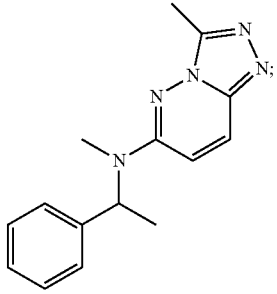

67
-continued
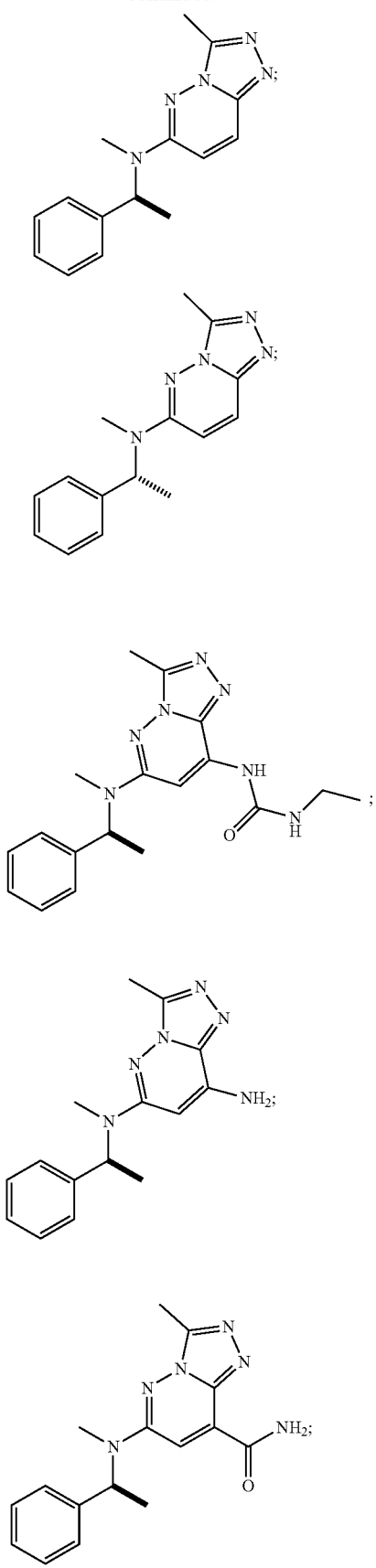
68
-continued
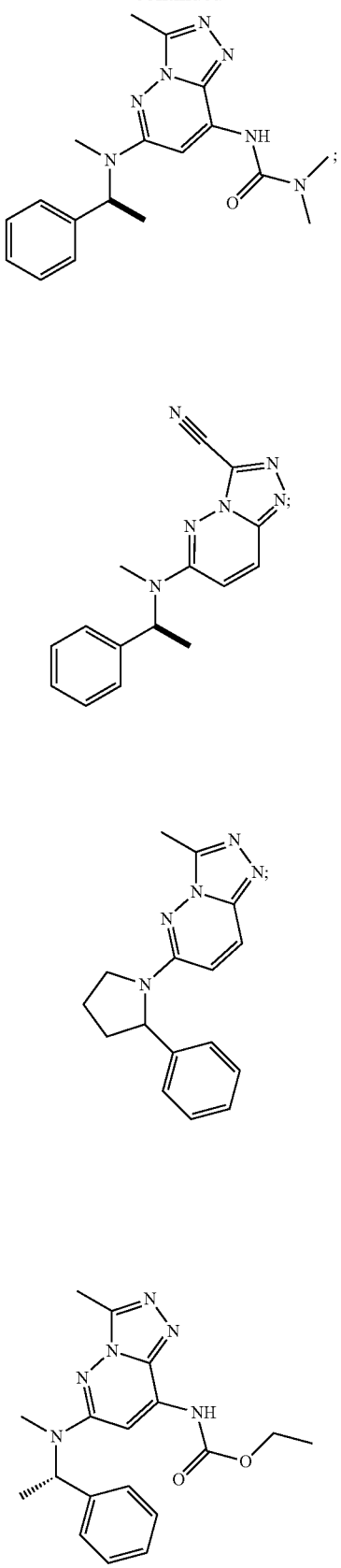

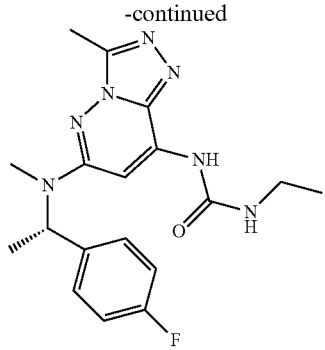

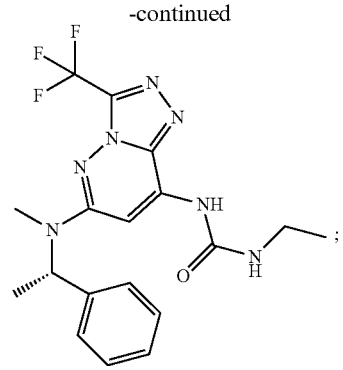

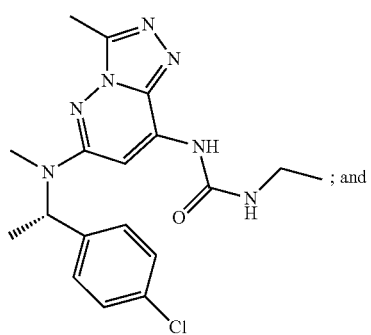

or a pharmaceutically acceptable salt thereof.

13. A composition comprising a compound according to claim 1, or a pharmaceutically acceptable salt thereof, and a pharmaceutically acceptable adjuvant, carrier, or vehicle.

14. The composition according to claim 13, further comprising an additional therapeutic agent.

15. A method of treating diffuse large B-cell lymphoma, Burkitt's lymphoma, Hodgkin's lymphoma, non-Hodgkin's lymphoma, multiple myeloma, primary central nervous system lymphoma, T-cell lymphoma, or acute myelogenous leukemia in a patient in need thereof, comprising the step of administering to said patient a compound according to claim 1, or a pharmaceutically acceptable salt thereof.

* * * * *